United States Patent
Hoey et al.

(10) Patent No.: US 7,169,144 B2
(45) Date of Patent: Jan. 30, 2007

(54) APPARATUS AND METHOD FOR CREATING, MAINTAINING, AND CONTROLLING A VIRTUAL ELECTRODE USED FOR THE ABLATION OF TISSUE

(75) Inventors: Michael F. Hoey, Shoreview, MN (US); Mark A. Christopherson, Shoreview, MN (US); Steven M. Goetz, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 141 days.

(21) Appl. No.: 10/699,548

(22) Filed: Oct. 31, 2003

(65) Prior Publication Data
US 2004/0092926 A1 May 13, 2004

Related U.S. Application Data

(63) Continuation of application No. 09/903,296, filed on Jul. 11, 2001, now Pat. No. 6,736,810, which is a continuation of application No. 09/347,635, filed on Jul. 6, 1999, now Pat. No. 6,409,722.

(60) Provisional application No. 60/091,959, filed on Jul. 7, 1998.

(51) Int. Cl.
*A61B 18/18* (2006.01)
(52) U.S. Cl. ........................... 606/34; 606/41
(58) Field of Classification Search ............. 606/1, 606/32–34, 41, 45–50; 607/101, 102; 600/424
See application file for complete search history.

(56) References Cited

U.S. PATENT DOCUMENTS 3,736,936 A   6/1973   Basiulis et al.
3,807,403 A   4/1974   Stumpf et al.
3,823,575 A   7/1974   Parel
3,823,718 A   7/1974   Tromovitch
3,827,436 A   8/1974   Stumpf et al.
3,830,239 A   8/1974   Stumpf (Continued)

OTHER PUBLICATIONS

A copy of PCT International Search Report mailed on Sep. 23, 2002 (10 pages).

(Continued)

*Primary Examiner*—Michael Peffley
(74) *Attorney, Agent, or Firm*—Dicke, Billig & Czaja, PLLC

(57) ABSTRACT

The present invention provides an apparatus and a method for producing a virtual electrode within or upon a tissue to be treated with radio frequency alternating electric current, such tissues including but not limited to liver, lung, cardiac, prostate, breast, and vascular tissues and neoplasms. An apparatus in accord with the present invention includes a supply of a conductive or electrolytic fluid to be provided to the patient, an alternating current generator, and a processor for creating, maintaining, and controlling the ablation process by the interstitial or surficial delivery of the fluid to a tissue and the delivery of electric power to the tissue via the virtual electrode. A method in accord with the present invention includes delivering a conductive fluid to a predetermined tissue ablation site for a predetermined time period, applying a predetermined power level of radio frequency current to the tissue, monitoring at least one of several parameters, and adjusting either the applied power and/or the fluid flow in response to the measured parameters.

43 Claims, 21 Drawing Sheets

U.S. PATENT DOCUMENTS

| | | |
|---|---|---|
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A * | 8/1994 | Nardella ............... 606/41 |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A * | 1/1995 | Jackson et al. ............ 606/1 |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,584,872 A | 12/1996 | LaFontaine et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |

| | | | | | | |
|---|---|---|---|---|---|---|
| 5,681,278 | A | 10/1997 | Igo et al. | 5,971,980 | A | 10/1999 | Sherman |
| 5,681,308 | A | 10/1997 | Edwards et al. | 5,971,983 | A | 10/1999 | Lesh |
| 5,687,723 | A | 11/1997 | Avitall | 5,993,447 | A | 11/1999 | Blewett et al. |
| 5,687,737 | A | 11/1997 | Branham et al. | 6,007,499 | A | 12/1999 | Martin et al. |
| 5,688,267 | A | 11/1997 | Panescu et al. | 6,012,457 | A | 1/2000 | Lesh |
| 5,690,611 | A | 11/1997 | Swartz et al. | 6,016,811 | A | 1/2000 | Knopp et al. |
| 5,697,536 | A | 12/1997 | Eggers et al. | 6,042,556 | A | 3/2000 | Beach et al. |
| 5,697,882 | A | 12/1997 | Eggers et al. | 6,063,081 | A | 5/2000 | Mulier |
| 5,697,925 | A | 12/1997 | Taylor | 6,071,279 | A | 6/2000 | Whayne et al. |
| 5,697,927 | A | 12/1997 | Imran et al. | 6,088,894 | A | 7/2000 | Oakley |
| 5,697,928 | A | 12/1997 | Walcott et al. | 6,096,037 | A | 8/2000 | Mulier |
| 5,713,942 | A | 2/1998 | Stern | 6,113,592 | A | 9/2000 | Taylor |
| 5,716,389 | A | 2/1998 | Walinsky et al. | 6,117,101 | A | 9/2000 | Diederich et al. |
| 5,718,241 | A | 2/1998 | Ben-Haim et al. | 6,120,496 | A | 9/2000 | Whayne et al. |
| 5,718,701 | A | 2/1998 | Shai et al. | 6,142,993 | A | 11/2000 | Whayne et al. |
| 5,720,775 | A | 2/1998 | Lanard | 6,142,994 | A | 11/2000 | Swanson et al. |
| 5,722,402 | A | 3/1998 | Swanson et al. | 6,152,920 | A | 11/2000 | Thompson et al. |
| 5,730,074 | A | 3/1998 | Peter | 6,161,543 | A | 12/2000 | Cox et al. |
| 5,730,127 | A | 3/1998 | Avitall | 6,165,169 | A * | 12/2000 | Panescu et al. ................. 606/1 |
| 5,730,704 | A | 3/1998 | Avitall | 6,165,174 | A | 12/2000 | Jacobs et al. |
| 5,733,280 | A | 3/1998 | Avitall | 6,217,528 | B1 | 4/2001 | Koblish et al. |
| 4,736,749 | A | 4/1998 | Lundback | 6,217,576 | B1 | 4/2001 | Tu et al. |
| 5,735,280 | A | 4/1998 | Sherman et al. | 6,224,592 | B1 | 5/2001 | Eggers et al. |
| 5,735,290 | A | 4/1998 | Sterman et al. | 6,231,518 | B1 | 5/2001 | Grabek et al. |
| 5,743,903 | A * | 4/1998 | Stern et al. .................... 606/31 | 6,235,020 | B1 | 5/2001 | Cheng et al. |
| 5,755,760 | A | 5/1998 | Maguire et al. | 6,235,024 | B1 | 5/2001 | Tu |
| 5,769,846 | A | 6/1998 | Edwards et al. | 6,237,605 | B1 | 5/2001 | Vaska et al. |
| 5,782,828 | A | 7/1998 | Chen et al. | 6,238,347 | B1 | 5/2001 | Nix et al. |
| 5,785,706 | A | 7/1998 | Bednarek | 6,238,393 | B1 | 5/2001 | Mulier et al. |
| 5,788,636 | A | 8/1998 | Curley | 6,245,061 | B1 | 6/2001 | Panescu et al. |
| 5,792,140 | A | 8/1998 | Tu et al. | 6,245,064 | B1 | 6/2001 | Lesh et al. |
| 5,797,960 | A | 8/1998 | Stevens et al. | 6,245,065 | B1 | 6/2001 | Panescu et al. |
| 5,800,428 | A | 9/1998 | Nelson et al. | 6,251,092 | B1 | 6/2001 | Qin et al. |
| 5,800,482 | A | 9/1998 | Pomeranz et al. | 6,251,128 | B1 | 6/2001 | Knopp et al. |
| 5,810,802 | A | 9/1998 | Panescu et al. | 6,266,551 | B1 * | 7/2001 | Osadchy et al. ............ 600/424 |
| 5,827,216 | A | 10/1998 | Igo et al. | 6,270,471 | B1 | 8/2001 | Hechel et al. |
| 5,836,947 | A | 11/1998 | Fleischman et al. | 6,293,943 | B1 | 9/2001 | Panescu et al. |
| 5,840,030 | A | 11/1998 | Ferek-Petric et al. | 6,296,619 | B1 | 10/2001 | Brisken et al. |
| 5,844,349 | A | 12/1998 | Oakley et al. | 6,302,880 | B1 | 10/2001 | Schaer |
| 5,846,187 | A | 12/1998 | Wells et al. | 6,311,692 | B1 | 11/2001 | Vaska et al. |
| 5,846,191 | A | 12/1998 | Wells et al. | 6,312,383 | B1 | 11/2001 | Lizzi et al. |
| 5,849,028 | A | 12/1998 | Chen | 6,314,962 | B1 | 11/2001 | Vaska et al. |
| 5,871,523 | A | 2/1999 | Fleischman et al. | 6,314,963 | B1 | 11/2001 | Vaska et al. |
| 5,871,525 | A | 2/1999 | Edwards et al. | 6,325,797 | B1 | 12/2001 | Stewart et al. |
| 5,873,845 | A | 2/1999 | Cline et al. | 6,328,736 | B1 | 12/2001 | Mulier |
| 5,876,399 | A | 3/1999 | Chia et al. | 6,332,881 | B1 | 12/2001 | Carner et al. |
| 5,879,295 | A | 3/1999 | Li et al. | 6,358,248 | B1 | 3/2002 | Mulier |
| 5,879,296 | A | 3/1999 | Ockuly et al. | 6,361,531 | B1 | 3/2002 | Hissong |
| 5,879,348 | A | 3/1999 | Owens et al. | 6,364,876 | B1 | 4/2002 | Erb et al. |
| 5,881,732 | A | 3/1999 | Sung et al. | 6,368,275 | B1 | 4/2002 | Sliwa et al. |
| 5,882,346 | A | 3/1999 | Pomeranz et al. | 6,371,955 | B1 | 4/2002 | Fuimaono et al. |
| 5,885,278 | A | 3/1999 | Fleischman | 6,383,151 | B1 | 5/2002 | Diederich et al. |
| 5,893,848 | A | 4/1999 | Negus et al. | 6,385,472 | B1 | 5/2002 | Hall et al. |
| 5,895,417 | A | 4/1999 | Pomeranz et al. | 6,398,792 | B1 | 6/2002 | O'Connor |
| 5,897,553 | A | 4/1999 | Mulier et al. | 6,409,722 | B1 | 6/2002 | Hoey et al. |
| 5,897,554 | A | 4/1999 | Chia et al. | 6,413,254 | B1 | 7/2002 | Hissong et al. |
| 5,899,898 | A | 5/1999 | Arless et al. | 6,419,648 | B1 | 7/2002 | Vitek et al. |
| 5,899,899 | A | 5/1999 | Arless et al. | 6,425,867 | B1 | 7/2002 | Vaezy et al. |
| 5,902,289 | A | 5/1999 | Swartz et al. | 6,430,426 | B2 | 8/2002 | Avitall |
| 5,904,711 | A | 5/1999 | Flom et al. | 6,440,130 | B1 | 8/2002 | Mulier |
| 5,906,580 | A | 5/1999 | Kline-Schoder et al. | 6,443,952 | B1 | 9/2002 | Mulier |
| 5,906,587 | A | 5/1999 | Zimmon | 6,447,507 | B1 | 9/2002 | Bednarek et al. |
| 5,906,606 | A | 5/1999 | Chee et al. | 6,461,314 | B1 | 10/2002 | Pant et al. |
| 5,908,029 | A | 6/1999 | Knudson et al. | 6,461,956 | B1 | 10/2002 | Hsuan et al. |
| 5,916,213 | A | 6/1999 | Haissaguerre et al. | 6,464,700 | B1 | 10/2002 | Koblish et al. |
| 5,916,214 | A | 6/1999 | Cosio et al. | 6,471,697 | B1 | 10/2002 | Lesh |
| 5,921,924 | A | 7/1999 | Avitall | 6,471,698 | B1 | 10/2002 | Edwards et al. |
| 5,921,982 | A | 7/1999 | Lesh et al. | 6,474,340 | B1 | 11/2002 | Vaska et al. |
| 5,927,284 | A | 7/1999 | Borst et al. | 6,475,216 | B2 | 11/2002 | Mulier |
| 5,928,191 | A | 7/1999 | Houser et al. | 6,477,396 | B1 | 11/2002 | Mest et al. |
| 5,931,810 | A | 8/1999 | Grabek | 6,484,727 | B1 | 11/2002 | Vaska et al. |
| 5,931,848 | A | 8/1999 | Saadat | 6,488,680 | B1 | 12/2002 | Francischelli |
| 5,954,661 | A | 9/1999 | Greenspon et al. | 6,502,575 | B1 | 1/2003 | Jacobs et al. |

| | | |
|---|---|---|
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,713 B2 * | 12/2004 | Bek et al. ............... 606/1 |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2003/0045872 A1 | 3/2003 | Jacobs |
| 2003/0144656 A1 | 7/2003 | Ocel |
| 2003/0191462 A1 | 10/2003 | Jacobs |
| 2003/0204185 A1* | 10/2003 | Sherman et al. ............ 606/41 |
| 2003/0216724 A1 | 11/2003 | Jahns |
| 2004/0015106 A1 | 1/2004 | Coleman |
| 2004/0015219 A1 | 1/2004 | Francischelli |
| 2004/0034346 A1* | 2/2004 | Stern et al. ............ 606/41 |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): 1-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

APPARATUS AND METHOD FOR CREATING, MAINTAINING, AND CONTROLLING A VIRTUAL ELECTRODE USED FOR THE ABLATION OF TISSUE

CROSS-REFERENCE TO RELATED APPLICATIONS

This application is a continuation of U.S. application Ser. No. 09/903,296 filed Jul. 11, 2001, now U.S. Pat. No. 6,736,810 which issued May 18, 2004; which is a continuation of U.S. application Ser. No. 09/347,635 filed on Jul. 6, 1999, now U.S. Pat. No. 6,409,722 which issued Jun. 25, 2002; which claims the benefit of U.S. Provisional Application Ser. No. 60/091,959 filed on Jul. 7, 1998.

FIELD OF THE INVENTION

The present invention relates generally to an apparatus and method of the creation of a virtual electrode. More particularly, the present invention relates to an apparatus and method of the creation of a virtual electrode, which is useful for the ablation of soft tissue and neoplasms.

BACKGROUND OF THE PRESENT INVENTION

The utilization of an electric current to produce an ameliorative effect on a bodily tissue has a long history, reportedly extending back to the ancient Greeks. The effects on bodily tissue from an applied electric current, and thus the dividing line between harmful and curative effects, will vary depending upon the voltage levels, current levels, the length of time the current is applied, and the tissue involved. One such effect resulting from the passage of an electric current through tissue is heat generation.

Body tissue, like all non-superconducting materials, conducts current with some degree of resistance. This resistance creates localized heating of the tissue through which the current is being conducted. The amount of heat generated will vary with the power P deposited in the tissue, which is a function of the product of the square of the current I and the resistance R of the tissue to the passage of the current through it ($P=I^2R$.).

As current is applied to tissue, then, heat is generated due to the inherent resistance of the tissue. Deleterious effects in the cells making up the tissue begin to occur at about 42° Celsius. As the temperature of the tissue increases because of the heat generated by the tissue's resistance, the tissue will undergo profound changes and eventually, as the temperature becomes high enough, that is, generally greater than 45° C., the cells will die. The zone of cell death is known as a lesion and the procedure followed to create the lesion is commonly called an ablation. As the temperature increases beyond cell death temperature, complete disintegration of the cell walls and cells caused by boiling off of the tissue's water can occur. Cell death temperatures can vary somewhat with the type of tissue to which the power is being applied, but generally will begin to occur within the range of 45° to 60° C., though actual cell death of certain tissue cells may occur at a higher temperature.

In recent times, electric current has found advantageous use in surgery, with the development of a variety of surgical instruments for cutting tissue or for coagulating blood. Still more recently, the use of alternating electric current to ablate, that is, kill, various tissues has been explored. Typically, current having a frequency from about 3 kilohertz to about 300 gigahertz, which is generally known as radiofrequency or radiofrequency (RF) current, is used for this procedure. Destruction, that is, killing, of tissue using an RF current is commonly known as radiofrequency ablation. Often radiofrequency ablation is performed as a minimally invasive procedure and is thus known as radiofrequency catheter ablation because the procedure is performed through and with the use of a catheter. By way of example, radiofrequency catheter ablation has been used to ablate cardiac tissue responsible for irregular heartbeat arrhythmias.

The prior art applications of current to tissue have typically involved applying the current using a "dry" electrode. That is, a metal electrode is applied to the tissue desired to be affected and a generated electric current is passed through the electrode to the tissue. A commonly known example of an instrument having such an operating characteristic is an electrosurgical instrument known as a "bovie" knife. This instrument includes a cutting/coagulating blade electrically attached to a current generator. The blade is applied to the tissue of a patient and the current passes through the blade into the tissue and through the patient's body to a metal base electrode or ground plate usually placed underneath and in electrical contact with the patient. The base electrode is in turn electrically connected to the current generator so as to provide a complete circuit.

As the current from the bovie knife passes from the blade into the tissue, the resistance provided by the tissue creates heat. In the cutting mode, a sufficient application of power through the bovie to the tissue causes the fluid within the cell to turn to steam, creating a sufficient overpressure so as to burst the cell walls. The cells then dry up, desiccate, and carbonize, resulting in localized shrinking and an opening in the tissue. Alternatively, the bovie knife can be applied to bleeding vessels to heat and coagulate the blood flowing therefrom and thus stop the bleeding.

As previously noted, another use for electrical instruments in the treatment of the body is in the ablation of tissue. To expand further on the brief description given earlier of the ablation of cardiac tissue, it has long been known that a certain kind of heart tissue known as sino-atrial and atrioventricular nodes spontaneously generate an electrical signal that is propagated throughout the heart along conductive pathways to cause it to beat. Occasionally, certain heart tissue will "misfire," causing the heart to beat irregularly. If the errant electrical pathways can be determined, the tissue pathways can be ablated and the irregular heartbeat remedied. In such a procedure, an electrode is placed via a catheter into contact with the tissue and then current is applied to the tissue via the electrode from a generator of RF current. The applied current will cause the tissue in contact with the electrode to heat. Power will continue to be applied until the tissue reaches a temperature where the heart tissue dies, thereby destroying the errant electrical pathway and the cause of the irregular heartbeat.

Another procedure using RF ablation is transurethral needle ablation, or TUNA, which is used to create a lesion in the prostate gland for the treatment of benign prostatic hypertrophy (BPH) or the enlargement of the prostate gland. In a TUNA procedure, a needle having an exposed conductive tip is inserted into the prostate gland and current is applied to the prostate gland via the needle. As noted previously, the tissue of the prostate gland heats locally surrounding the needle tip as the current passes from the needle to the base electrode. A lesion is created as the tissue heats and the destroyed cells may be reabsorbed by the body, infiltrated with scar tissue, or just become non-functional.

While there are advantages and uses for such "dry" electrode instruments, there are also several notable disadvantages. One of these disadvantages is that during a procedure coagulum—dried blood cells and tissue cells—will form on the electrode engaging the tissue. Coagulum acts as an insulator and effectively functions to prevent current transfer from the blade to the tissue. This coagulum "insulation" can be overcome with more voltage so as to keep the current flowing, but only at the risk of arcing and injuring the patient. Thus, during surgery when the tissue is cut with an electrosurgical scalpel, a build-up of coagulated blood and desiccated tissue will occur on the blade, requiring the blade to be cleaned before further use. Typically, cleaning an electrode/scalpel used in this manner will involve simply scraping the dried tissue from the electrode/scalpel by rubbing the scalpel across an abrasive pad to remove the coagulum. This is a tedious procedure for the surgeon and the operating staff since it requires the "real" work of the surgery to be discontinued while the cleaning operation occurs. This procedure can be avoided with the use of specially coated blades that resist the build up of coagulum. Such specialty blades are costly, however.

A second disadvantage of the dry electrode approach is that the electrical heating of the tissue creates smoke that is now known to include cancer-causing agents. Thus, preferred uses of such equipment will include appropriate ventilation systems, which can themselves become quite elaborate and quite expensive.

A further, and perhaps the most significant, disadvantage of dry electrode electrosurgical tools is revealed during cardiac ablation procedures. During such a procedure, an electrode that is otherwise insulated but having an exposed, current carrying tip is inserted into the heart chamber and brought into contact with the inner or endocardial side of the heart wall where the ablation is to occur. The current is initiated and passes from the current generator to the needle tip electrode and from there into the tissue so that a lesion is created. Typically, however, the lesion created by a single insertion is insufficient to cure the irregular heartbeat because the lesion created is of an insufficient size to destroy the errant electrical pathway. Thus, multiple needle insertions and multiple current applications are almost always required to ablate the errant cardiac pathway, prolonging the surgery and thus increasing the potential risk to the patient.

This foregoing problem is also present in TUNA procedures, which similarly requires multiple insertions of the needle electrode into the prostate gland. Failing to do so will result in the failure to create a lesion of sufficient size such that the procedure produces a beneficial result. As with radiofrequency catheter ablation of cardiac tissue, then, the ability to create a lesion of the necessary size to alleviate BPH symptoms is limited and thus requires multiple insertions of the electrode into the prostate.

A typical lesion created with a dry electrode using RF current and a single insertion will normally not exceed one centimeter in diameter. This small size—often too small to be of much or any therapeutic benefit—stems from the fact that the tissue surrounding the needle electrode tends to desiccate as the temperature of the tissue increases, leading to the creation of a high resistance to the further passage of current from the needle electrode into the tissue, all as previously noted with regard to the formation of coagulum on an electrosurgical scalpel. This high resistance—more properly termed impedance since typically an alternating current is being used—between the needle electrode and the base electrode is commonly measured by the RF current generator. When the measured impedance reaches a predetermined level, the generator will discontinue current generation. Discontinuance of the ablation procedure under these circumstances is necessary to avoid injury to the patient.

Thus, a typical procedure with a dry electrode may involve placing the needle electrode at a first desired location; energizing the electrode to ablate the tissue; continue applying current until the generator measures a high impedance and shuts down; moving the needle to a new location closely adjacent to the first location; and applying current again to the tissue through the needle electrode. This cycle of electrode placement, electrode energization, generator shut down, electrode re-emplacement, and electrode re-energization, will be continued until a lesion of the desired size has been created. As noted, this increases the length of the procedure for the patient. Additionally, multiple insertions increases the risk of at least one of the placements being in the wrong location and, consequently, the risk that healthy tissue may be undesirably affected while diseased treatment may be left untreated. The traditional RF ablation procedure of using a dry ablation therefore includes several patient risk factors that both patient and physician would prefer to reduce or eliminate.

The therapeutic advantages of RF current could be increased if a larger lesion could be created safely with a single positioning of the current-supplying electrode. A single positioning would allow the procedure to be carried out more expeditiously and more efficiently, reducing the time involved in the procedure. Larger lesions can be created in at least two ways. First, simply continuing to apply current to the patient with sufficiently increasing voltage to overcome the impedance rises will create a larger lesion, though almost always with undesirable results to the patient. Second, a larger lesion can be created if the current density, that is, the applied electrical energy, could be spread more efficiently throughout a larger volume of tissue. Spreading the current density over a larger tissue volume would correspondingly cause a larger volume of tissue to heat in the first instance. That is, by spreading the applied power throughout a larger tissue volume, the tissue would heat more uniformly over a larger volume, which would help to reduce the likelihood of generator shutdown due to high impedance conditions. The applied power, then, will cause the larger volume of tissue to be ablated safely, efficiently, and quickly.

Research conducted under the auspices of the assignee of the present invention has focused on spreading the current density throughout a larger tissue volume through the creation, maintenance, and control of a "virtual electrode" within or adjacent to the tissue to be ablated. A virtual electrode can be created by the introduction of a conductive fluid, such as isotonic or hypertonic saline, into or onto the tissue to be ablated. The conductive fluid will facilitate the spread of the current density substantially equally throughout the extent of the flow of the conductive fluid, thus creating an electrode—a virtual electrode—substantially equal in extent to the size of the delivered conductive fluid. RF current can then be passed through the virtual electrode into the tissue.

A virtual electrode can be substantially larger in volume than the needle tip electrode typically used in RF interstitial ablation procedures and thus can create a larger lesion than can a dry, needle tip electrode. That is, the virtual electrode spreads or conducts the RF current density outward from the RF current source—such as a current carrying needle, forceps or other current delivery device—into or onto a larger volume of tissue than is possible with instruments that rely on the use of a dry electrode. Stated otherwise, the creation of the virtual electrode enables the current to flow with reduced resistance or impedance throughout a larger volume of tissue, thus spreading the resistive heating created by the current flow through a larger volume of tissue and thereby creating a larger lesion than could otherwise be created with a dry electrode.

While the efficacy of RF current ablation techniques using a virtual electrode has been demonstrated in several studies, the currently available instruments useful in such procedures lags behind the research into and development of hoped-for useful treatment modalities for the ablation of soft tissue and malignancies. Thus, to perform current research procedures it is necessary to provide separately both a fluid pump and an RF current generator. The fluid pump requires an electrical connection and fluid conduits running from the fluid supply to the fluid delivery instrument. The generator also requires electrical connections and electric lines running from the generator to the surgical instrument, as well as a return electrical line from the ground plate when a monopolar electrode is used. Use of these systems is thus hampered by the many fluid and electrical lines surrounding the operating theater, all of which can easily become entangled and complicate their use.

Further, currently available generators provide limited control over the power application to the tissue. For example, such generators, which are often designed for cardiac ablation procedures, provide for an immediate or nearly immediate cessation of power upon the occurrence of equipment defined high impedance conditions. These generators are thus unable to operate continuously—and therefore unable to provide the most expeditious, efficient therapy—when operating in the presence of fleeting high impedance conditions. Consequently, the presently available generators will automatically shut off when such a condition occurs even though continued application of RF power would otherwise be safe. The generator must then be restarted, which is not only an unnecessary annoyance but also prolongs the procedure since such shutdowns can occur more than once during any one ablation procedure.

It would be desirable to have an apparatus and method capable of creating, maintaining, and controlling a virtual electrode while providing a controlled application of tissue ablating RF electric current to a tissue of interest so as to produce a lesion of desired size and configuration. Preferably, such an apparatus will be capable of adjusting the applied current and fluid flow in accord with the measured impedance of the tissue and/or the temperature of the tissue being ablated. It would also be desirable to have such an apparatus and method capable of continuing operation in the presence of transient high impedance conditions.

SUMMARY OF THE INVENTION

It is an object of the present invention to provide a new and improved apparatus and method that is not subject to the foregoing disadvantages.

It is another object of the present invention to provide an integrated conductive fluid supply and radio frequency current generator.

It is still another object of the present invention to provide a device having an integrally controlled and operated conductive fluid supply and radio frequency current generator that controls the applied power and rate of conductive fluid infusion in response to the measured impedance of the tissue being ablated.

It is yet another object of the present invention to provide an integrally controlled and operated conductive fluid supply and radio frequency current generator that controls the applied power and rate of conductive fluid infusion in response to the measured impedance transients.

It is still yet another object of the present invention to provide an integrally controlled and operated conductive fluid supply and radio frequency current generator that selectively controls the applied power and rate of conductive fluid infusion in response to the measured temperature of the tissue being ablated.

It is a further object of the present invention to provide a method for treating a patient with RF current via a virtual electrode to produce a lesion of a predetermined size.

The foregoing objects of the present invention are achieved by an apparatus and a method for producing a virtual electrode within or upon a tissue to be treated with radio frequency alternating electric current, such tissues including but not limited to liver, lung, cardiac, prostate, breast, and vascular tissues and neoplasms. An apparatus in accord with the present invention will include a supply of a conductive or electrolytic fluid to be provided to the patient, an alternating current generator, and a processor for creating, maintaining, and controlling the ablation process by the interstitial or surficial delivery of the fluid to a tissue and the delivery of electric power to the tissue via the virtual electrode.

The control of the virtual electrode and the ablation procedure is accomplished in response to measured temperatures at pre-determined distances from a current delivery device and/or measured impedances over pre-determined time intervals. The ablation procedure is adjusted due to transient impedance rises related to the novel apparatus and its operation as well as due to those impedance and temperature changes related to the flow of current from the virtual electrode through the tissue being treated. Such an apparatus in accord with the present invention will also preferably include a display for visualizing predetermined operational parameters and for visualizing the ongoing operation of the virtual electrode and the apparatus during an ablation procedure.

In addition, an apparatus in accord with the present invention will also preferably include an input apparatus such as a rotary encoder and mouse-type of device, a touch screen useful in the form of a menu-driven icon system, and/or a keyboard. The input apparatus is provided to allow the operator to input predetermined information, such as tissue type to be ablated, desired lesion size, type of electrolytic fluid being used, the particular surgical instrument being used, and any other desired parameter of interest.

An apparatus in accord with the present invention may also include one or more additional fluid administration systems providing a controlled delivery of at least a second fluid to the patient during an ablation procedure. Such a fluid may be provided for maintaining the temperature of the tissue surrounding the tissue to be ablated at a non-harmful temperature, such as by directly cooling the tissue. Alternatively, an insulating fluid such as dextrose may be infused into the tissue surrounding the tissue ablation site, thus increasing the impedance of this surrounding tissue to prevent current passage therethrough and thereby diminishing the likelihood of unwanted heating of this surrounding tissue.

A method in accord with the present invention will include the steps of delivering a conductive fluid to a predetermined tissue ablation site to be ablated for a predetermined time period that may range from zero seconds to about ten minutes, preferably within the range of zero to sixty seconds, thereby creating a virtual electrode, applying a predetermined power level of radio frequency current to the tissue via the virtual electrode, monitoring at least one of several parameters (including but not limited to impedance, tissue temperature at one or more pre-selected distances from the current delivery device, the applied power, and fluid flow), and adjusting either the applied power and/or the fluid flow in response to the measured parameters. The method may also include the placement of a current delivery device within the tissue ablation site, such as substantially at the center thereof, and/or the placement of at least one additional temperature sensor in tissue whose ablation is not desired yet is adjacent to the predetermined ablation site. By way of example only, where an increase of impedance of predetermined size occurs within a predetermined time period the applied power may be automatically reduced by a predetermined amount for a predetermined period of time. By way of yet another example, when a tissue target temperature is reached, the applied power may be reduced to maintain the temperature at the target temperature and reduce the likelihood of increasing the tissue temperature of the ablation site above the target temperature. By way of another example, the flow of conductive fluid to the tissue ablation site can be increased or decreased in response to one or more of the measured parameters (temperature, impedance, etc.).

The foregoing objects of the invention will become apparent to those skilled in the art when the following detailed description of the invention is read in conjunction with the accompanying drawings and claims. Throughout the drawings, like numerals refer to similar or identical parts.

DETAILED DESCRIPTION OF THE INVENTION

Figure 1:
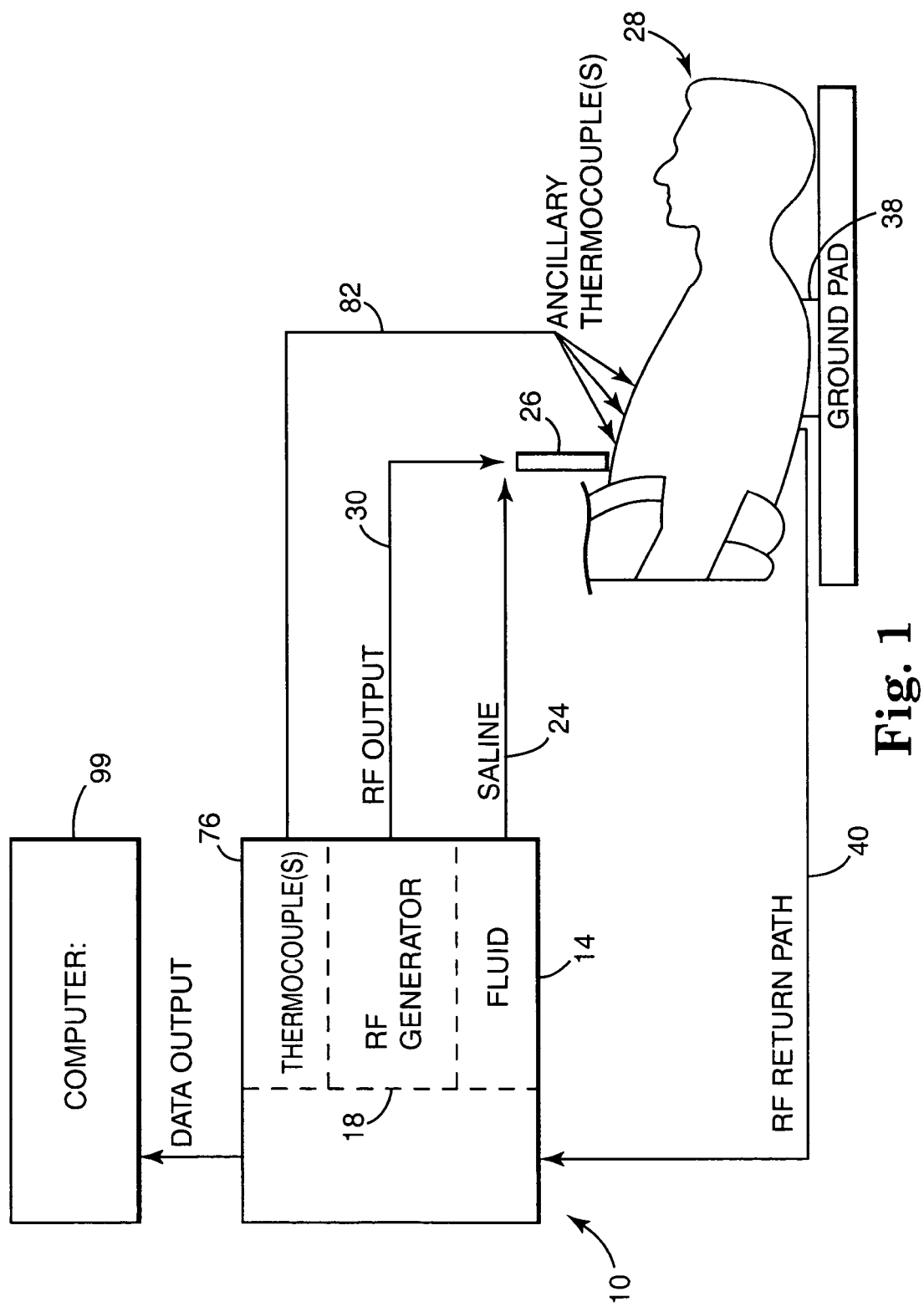
FIG. 1 illustrates in an overview of an apparatus in accord with the present invention in an operational setting with a human patient.

Referring now to FIGS. 1–4, a Virtual Electrode Thermal Ablation Device (VETAD) 10 in accord with the present invention will be described. VETAD 10 comprises a housing 12 for receiving a conductive fluid supply 14, a generator 18 for generating radio frequency current, a microprocessor 20 for, among other features, substantially simultaneously controlling the flow rate of fluid 14 supplied by pump 16 and the power supplied by generator 18, and a display/control panel 22.

Conductive fluid is transferred from supply 14 via a fluid line 24 to a surgical instrument 26 and then to a patient 28. A pump 16, which is preferably a syringe-type pump of the kind presently manufactured by Kloehn Corporation, may be used to assist in the transfer of conductive fluid from the fluid supply to the patient. A syringe-type pump generally includes a piston 17 that will extend in the direction of the arrow 17a to engage the syringe plunger 17b of a syringe 17c holding the conductive fluid to be used in the RF therapy procedure. Syringe 17c is held within a recess 17d of housing 12, the recess 17d being configured to accept syringes having standard configurations. During operation of VETAD 10 the piston 17 will be moved to engage the syringe plunger 17b and push the plunger 17b through the syringe barrel 17e of syringe 17c, thus forcing the conductive fluid out of the syringe 17c into the fluid line 24. It will be observed that the syringe 17c is disposed such that the extension of the piston 17 is generally horizontal, though other orientations would work equally well with the present invention.

More generally and preferably, pump 16 is of the type where the fluid in the supply 14 does not come into contact with the mechanisms of the pump 16. With this type of pump the sterility of the conductive fluid can be maintained until delivered to the patient 28. Another such type of pump, then, that could also be used with the present invention is a flexible tube pump. The fluid line 24 will generally thus take the form of a flexible tube that extends either from the supply 14 to the instrument 26 if pump 16 is a syringe-type pump, or from the supply 14 through the pump 16, and out to the surgical instrument 26 if pump 16 is a flexible tube type of pump. As part of a method of treating a patient according to the present invention, then, the fluid supply 14 may comprise a container, such as a syringe or flexible bag, holding a conductive or electrolytic fluid, such as isotonic or hypertonic saline. Desirably, the fluid supply 14 and the fluid line 24 will be supplied as new, sterile, disposable equipment for each procedure, thereby substantially reducing the risk of contamination of the fluid or of infecting the patient. With a syringe pump, the fluid supply will comprise a syringe filled with a conductive fluid. The syringe may be pre-filled or filled manually by a clinician or the like prior to an ablation procedure.

Generator 18 will supply radio frequency alternating current to the surgical instrument 26 via electrical line 30. The operation of generator 18 is controlled by microprocessor 20, which communicates with generator 18 as will be described below. Microprocessor 20 also communicates with pump 16 via a line 34. Microprocessor 20 is in turn controlled by its preprogrammed software and by the inputs received from the display/control panel 22 over line 36.

Surgical instrument 26 may take various forms. Minimally, however, the instrument 26 will be capable of delivering surficially or interstitially an RF current ablating fluid to create the virtual electrode and will include means for applying the current to the tissue via the virtual electrode. For example, instrument 26 may comprise a straight metal needle having an interior fluid transmitting lumen. Such a needle will be insulated except for a predetermined length at the distal or patient end thereof and will have a single aperture at the distal end and/or one or more apertures disposed around the needle shaft for the infusion of the conductive fluid 14 from the needle lumen into the tissue to create the virtual electrode. In addition, surgical instrument 26 can comprise other forms of instruments useful in the delivery of both radio frequency current and a conductive fluid to a patient. Such instruments would include needles of various configurations, catheter or guide wire assemblies, blades, and forceps, as well as any other future developed instruments that can supply a conductive fluid to the tissue to be ablated along with RF current applied either to the tissue and/or the conductive fluid.

A VETAD 10 in accord with the present invention will preferably have the capability of providing a power output of 0.1 watt to about 200 watts at a frequency of between about 350 kHz and 700 KHZ, preferably about 475 KHZ, and of incrementing or decrementing the power output by about 1 watt intervals. VETAD 10 will preferably be able to deliver the desired power level into resistive loads in a range of about ten (10) ohms to about five hundred (500) ohms. In addition to creating a virtual electrode and providing an ablative radio frequency current to a patient via the virtual electrode, VETAD 10 will monitor a variety of variables involved in an RF current ablation procedure, including but not limited to (1) the temperature of the tissue being ablated or surrounding the tissue being ablated via one or more thermocouples; (2) the occurrence of an electrical arc detected by a spike in the measured voltage; (3) the applied power; (4) the flow rate of the conductive fluid; and (5) the impedance between the virtual electrode and the ground or base plate.

Pump 16 of VETAD 10 will deliver conductive fluid to the ablation site at flow rates of about 0.1 to 10.0 cubic centimeters per minute in increment sizes of 0.1 cubic centimeters per minute. Where a syringe pump is used, VETAD 10 will be configured so that the amount of conductive fluid remaining in the barrel of the syringe can be determined via the relative position of the piston 17 of the pump. In one embodiment of the present invention, the VETAD 10 will provide an indication of low fluid volume remaining when piston travel has reached ninety percent (90%) of maximum travel and when the fluid has been exhausted as indicated by the piston travel reaching the one hundred percent (100%) maximum travel distance.

Figure 2:
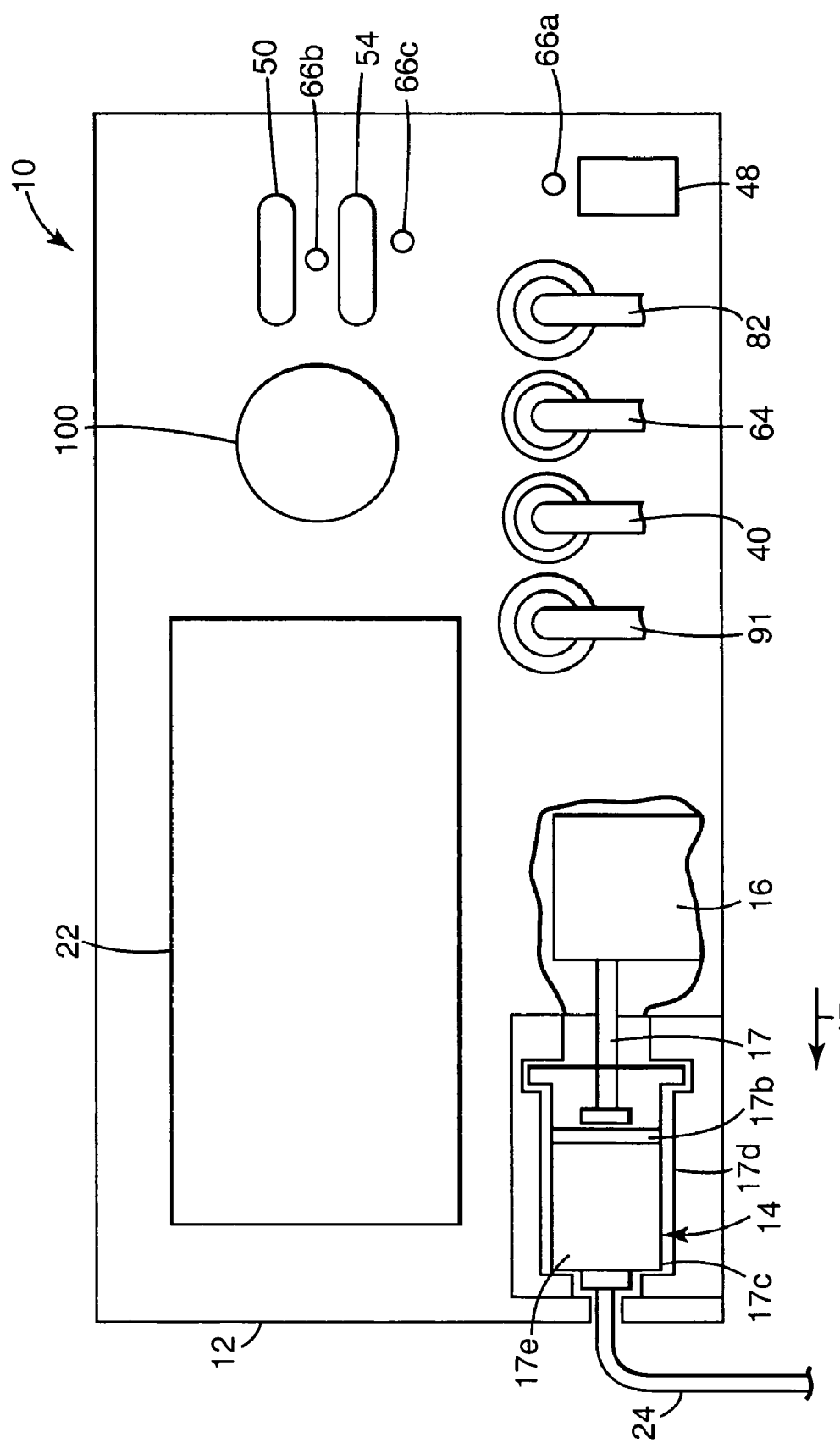
FIG. 2 shows an example of a housing, display, and controls which may be used with the present invention.
Figure 3:
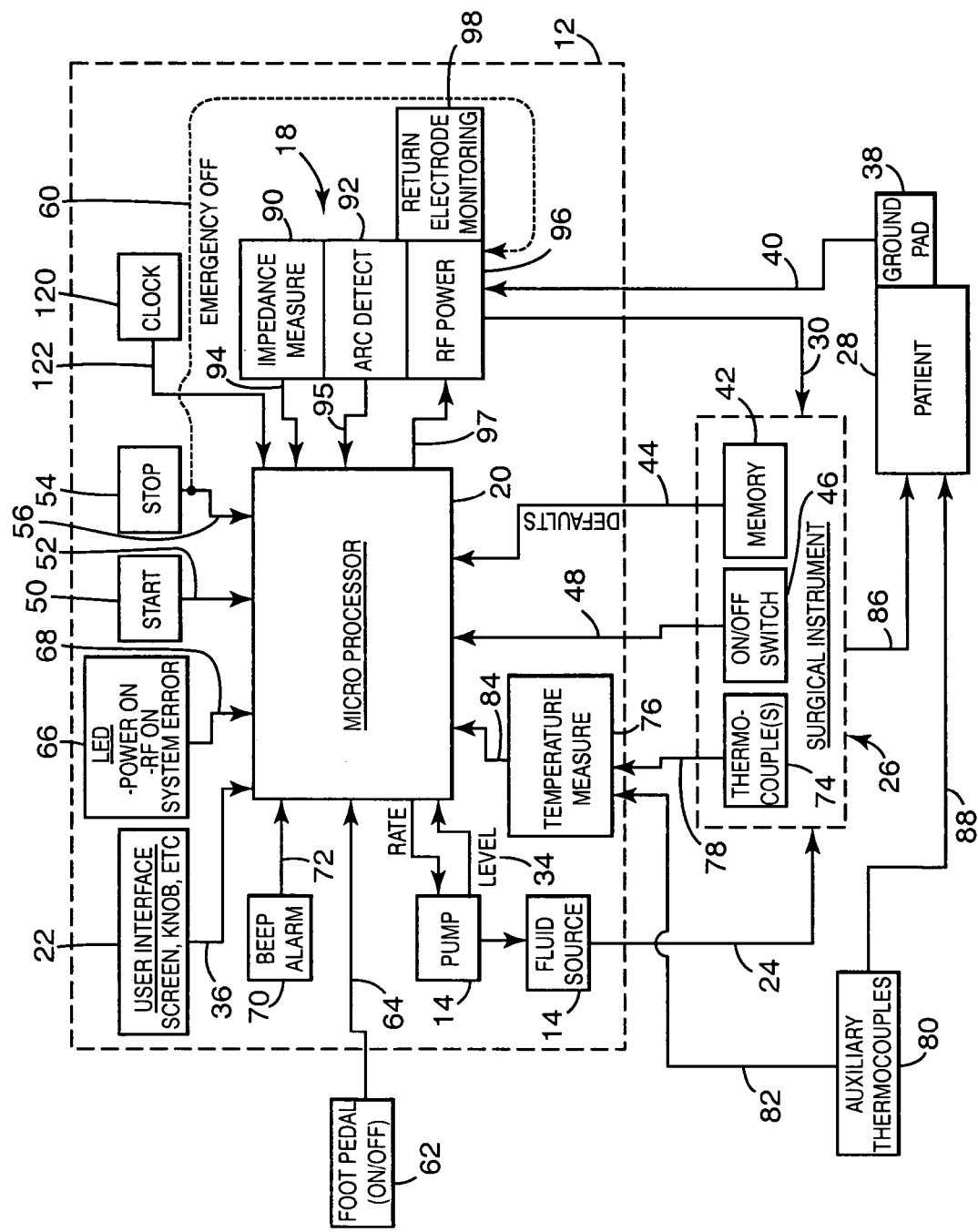
FIG. 3 is a schematic representation of an apparatus in accord with the present invention.

As illustrated in FIG. 2, the housing 12 will include separate ports for the fluid line 24 and the line 30 (desirably forming part of line 91 as will be explained below). If desired, however, a single port for provision of both the conductive fluid and the radio frequency current to the instrument 26 could be provided. Furthermore, it should be noted that FIGS. 1 and 3 illustrate the use of a monopolar surgical instrument 26 in association with VETAD 10. With such a use, a ground pad 38 will be placed in electrical contact with the patient 26 and a line 40 will extend between the ground pad 38 and VETAD 10 so as to provide a complete electrical circuit from VETAD 10 to the patient 28 and back to VETAD 10 for the current produced by VETAD 10. More generally, the ground pad provides a return electrode completing the electrical circuit. Bi-polar instruments are also known in the art and when such a bi-polar instrument would be used with the present invention 10 the complete electrical circuit would be provided by a return electrode within the instrument 26. With such a bipolar instrument a return path for the RF current from the generator 18 would be provided by the return electrode within instrument 26 and line 30.

The connectors used to couple the instrument 26 to VETAD 10 can take several different forms. For example, the pin connections between instrument 26 and VETAD 10 could provide the VETAD 10 with an identification. Varying surgical instruments could then use different pins to indicate to VETAD 10 which instrument is being used. By way of example only, a nine-pin port could be used and the surgical instruments could use one or more of the pins to communicate with the VETAD 10 and provide its identity and/or default operating parameters. VETAD 10 would then establish the initial operating parameters for an ablation procedure based upon the instrument's identity—for example, a straight needle versus a helical needle. That is, with this form of instrument, the default and desired operating parameters would be stored in the memory associated with the microprocessor 20 for a particular disposable surgical instrument 26, the microprocessor "recognizing" the disposable by the pin configuration thereof.

Alternatively, a standard connector could be used for all disposable surgical instruments 26. Each instrument 26 can then include a pre-programmed microchip or memory chip 42 that would communicate with the microprocessor 20 over a line 44 and that would provide VETAD 10 with identifying characteristics and other relevant information such as default operating parameters relating to power, temperature, and fluid flow upon receiving the appropriate inquiry signal from VETAD 10. Providing the instruments 26 with a memory chip 42 will also enable each instrument 26 to be given a unique identifier that the microprocessor 20 can use for tracking the number of uses of the particular instrument 26. For example, the microprocessor can be programmed to limit the total of number of times that RF current is sent through the instrument, the total amount of time that the instrument 26 is subjected to RF current, and the time frame within which an instrument 26 is used. By way of example only and not to limit the present invention in any manner, the defaults for a particular instrument 26 may be 10 distinct start-ups, a total of 10 minutes of ablation time, and a four hour time period in which the instrument must be used. The instruments 26 may include on/off switches 46 that would communicate with microprocessor 20 to allow the surgeon to start/stop the procedure and/or control the RF power during a procedure. Regardless of the form of the connection between the instrument 26 and VETAD 10 then, instrument 26 and its connector to VETAD 10 will preferably be disposable, with the disposal time being determined based upon the number of ablation procedures begun or the expiration of a predetermined time period following first use of the instrument. This will facilitate the use of sterile procedures and reduce the risk of secondary infections to the patient.

Referring now to FIGS. 2 and 3, VETAD 10 will include a power on/off switch 48 for VETAD 10 and an on or start switch 50 connected to microprocessor 20 by a line 52 and an off or stop switch 54 connected to microprocessor 20 by a line 56 and to RF generator 18 by a line 60. Thus, switch 48 will turn the apparatus 10 on while switch 50 will initiate the flow of RF current from the generator 18 to the patient 28. In addition, VETAD 10 may include a foot pedal 62 connected to microprocessor 20 by a line 64. Switch 54 will also function as an emergency off for disabling or shutting off the generator 18 directly. Line 64 could, if desired, be a mechanical or pneumatic linkage or switch if desired.

Regarding the operation of the foot pedal 62, microprocessor 20 will be programmed such that if the foot pedal 62 is depressed while the generator 18 is inactive but ready for operation, the therapy procedure shall begin. Releasing the foot pedal within a predetermined period of time, say three (3) seconds, will terminate the therapy session. Keeping the foot pedal 62 depressed for the predetermined period of time, such as three seconds, will cause the control to latch and the therapy will continue even if the pedal is released. Pressing on the foot pedal 62 when the generator 18 is operating will terminate the therapy session. As noted, any surgical instrument 26 may also include an on/off button 46 that operates in the same manner as the foot pedal 62.

VETAD 10 may also include visual indicators for indicating various operating conditions thereof. For example, VETAD 10 may include one or more light emitting diodes (LEDs) 66 (FIG. 2) that communicate with microprocessor 20 over a line 68. In one embodiment of the present invention three such LEDs may be used. For example, an LED 66a may be used to indicate that power is being supplied to the apparatus 10; and LED 66b may be used to indicate that RF power is being generated by generator 18; and an LED 66c may be used to indicate a system error or failure of some kind. An auditory indicator of system operation may also be provided by a "beep" alarm 70 that communicates with microprocessor 20 over a line 72. Beeper 70 may sound for example, during generation of RF power by generator 18 or to warn of an error condition.

Referring still primarily to FIG. 3, it will be observed that the surgical instrument 26 may include one or more thermocouples 74 that communicate with a temperature measurement circuit 76 of VETAD 10 over a line 78. In addition VETAD 10 may include one or more auxiliary thermocouples 80 that are placed at selected tissue locations as will be explained further below. Thermocouples 80 communicate with temperature measurement circuit 76 over a line 82. Circuit 76 in turn communicates with microprocessor 20 over a line 84. Thermocouples 74 and 80 are provided for providing temperature measurements at selected tissue locations to indicate the progress of the ablation therapy. That is, by monitoring the temperature of the tissue, it can be determined if the tissue is being ablated and whether healthy tissue whose ablation is not desired is being affected. Circuit 76 may take the form of a single circuit or it could comprise two identical circuits such that the apparatus 10 provides a redundant safety feature. With a double circuit the thermocouples would be divided into two groups of thermocouples with one group providing temperature indicating signals to one circuit and the other group providing temperature indicating signals to the other circuit. With a dual circuit structure if one circuit failed the other will remain operational and the therapy will continue. Shutdown of the therapy and the apparatus 10 would occur with failure of both of the dual circuits of the temperature measurement circuit 76. Stated otherwise, a double circuit would provide an additional patient safety feature. For example, a surgical instrument 26 could comprise a straight or helical needle with two thermocouples or temperature sensors thereon. Both thermocouples would provide signals indicative of temperature to the circuit 76 and would output both sets to the microprocessor 20. If either set of signals indicated a therapy failure or discontinuance state, such as one of them reaching and exceeding the primary temperature threshold, the application of RF power would be discontinued. In this way, one circuit could fail and provide false readings of low temperatures, but patient safety would be maintained by the second circuit providing accurate temperature signals to the microprocessor 20.

It will be understood line 86 illustrates the engagement of the surgical instrument 26 with the patient 28 and that the line 88 illustrates the engagement of the auxiliary thermocouples 80 with the patient 28. It will further be understood that the lines 30, 44, 48, and 78 extending between the instrument 28 and the VETAD 10 will typically be supplied by a single connection 91 (FIG. 2) with VETAD 10.

The generator 18 will include an impedance measurement circuit 90 that communicates with microprocessor 20 over a line 92 and an arc detection circuit 94 that communicates with microprocessor 20 over a line 95. Generator 18 will also include the RF power generation circuit 96, which communicates with microprocessor 20 over a line 97. Preferably, generator 18 will also include a circuit 98 to monitor the return electrode—the ground pad 38. In one embodiment of the present invention, ground pad 38 will comprise a split electrode. Circuit 98 will monitor the impedance between the split electrodes to reduce the likelihood of patient injury due to a high power flow through only one of the electrodes. It should be understood that although the present invention is shown as having generator 18 include the impedance measurement circuit 90, the arc detection circuit 92, and the RF power generation circuit 96, circuits 90 and 92 could be partially hardware and partially software running in microprocessor 20.

Referring to FIG. 1, it will be understood that VETAD 10 will include the appropriate data output port, such as an RS-232 port to enable the attachment of external devices, such as a computer 99 to provide for downloading data in real time or at a later date and/or permanent storage of data gathered during an ablation therapy session. It will be understood that computer 99 may be remotely located from VETAD 10 and communicate therewith over a telephone or other data transfer line.

Figure 4:
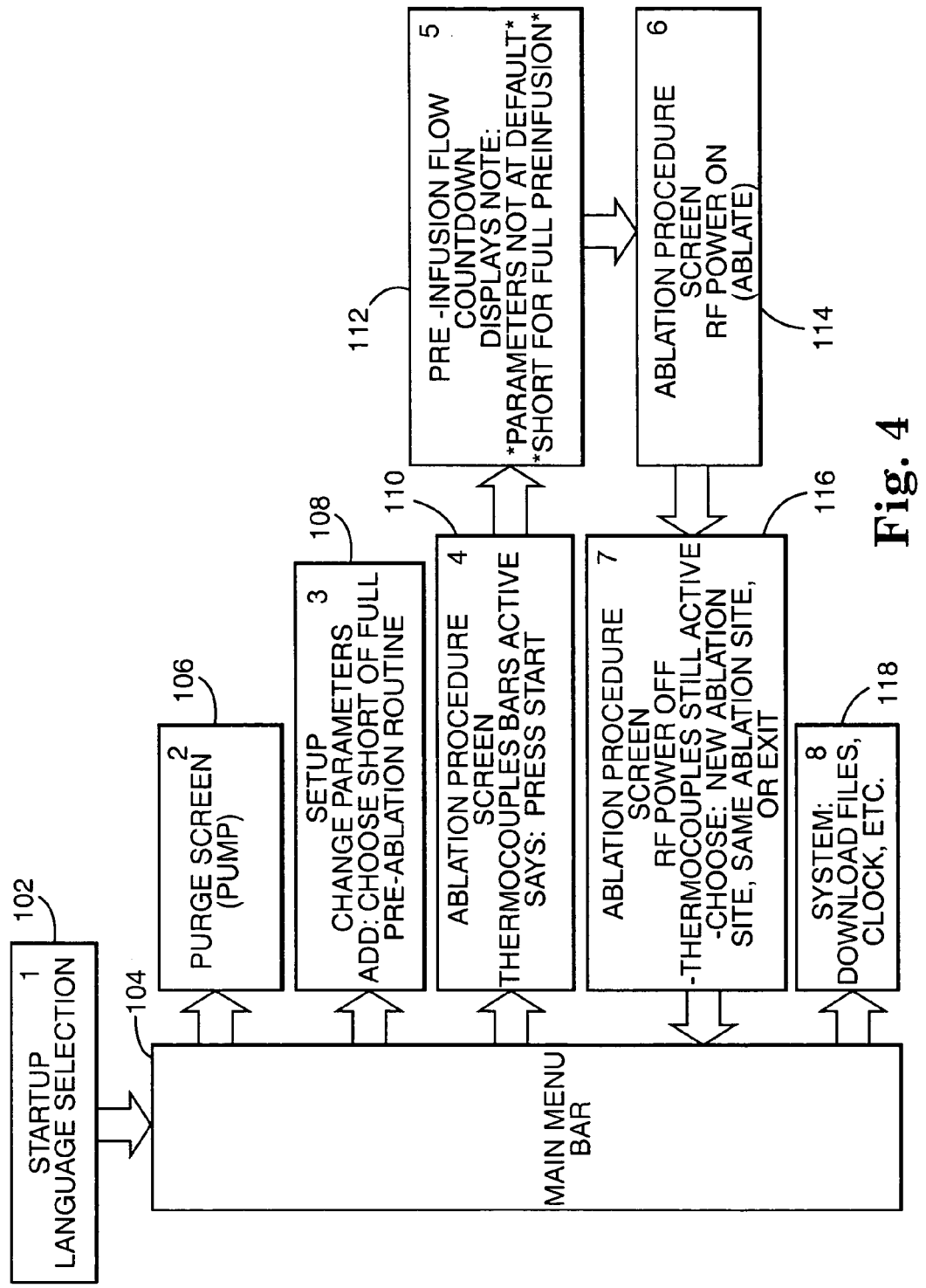
FIG. 4 schematically illustrates display screens forming a user or operator interface for use in an apparatus in accord with the present invention.

Referring now to FIGS. 2 and 4, the various user interface screens that may be displayed in display 22 is shown. Display 22 may include an electroluminscent display or a liquid crystal diode (LCD) or similar display. Display 22 further includes a rotary knob/encoder 100. In using a display 22, the rotary encoder will be rotated to change the display between the pump, setup, procedure, and system to display predetermined parameters relating to operation of the apparatus 10. The display/user interface will enable the operator to select and adjust parameters for a specific tissue ablation, purge the fluid lines, download or clear log files of an ablation procedure(s), adjust fluid flow rates and RF power levels, adjust maximum temperatures for the various monitored temperatures, etc.

At startup, a language selection screen 102 will appear on the main menu bar 104 to allow the operator to select a particular language for use during the procedure. The knob 100 can be rotated to the appropriate language and then pushed to select a language. Following the selection of a language, other user interface screens can be selectively displayed. Such screens may include a purge screen 106, a setup screen 108, an ablation procedure start screen 110, a pre-infusion flow screen 112, an ablation procedure screen (power on) 114, an ablation procedure screen 116 (power off), and a system screen 118. During the display of the various user interface screens the operator will be able to select the various operation parameters, such as power level, infusion rate, temperature thresholds, pre-ablation infusion rates and times, and new placements or restarts of the procedure with the same placement of the instrument to name a few. In addition, an embodiment of the present invention may also allow the operator to specify the type of tissue being ablated. During an ablation procedure the display 22 will show the temperatures measured by the thermocouples 74 and 80, the infusion rate, the amount of conductive fluid remaining in the supply the power level, the impedance, and the unique identifier of the particular instrument 28 if there is one.

Display 22 will also preferably indicate a plurality of levels of alarm conditions, for example, for a warning state, a therapy failure state, and a system failure state, as indicated by light emitting diode 66. Preferably, each alarm condition will be made known by the lighting of the particular associated LED and a distinctive sound or tone produced by an appropriate speaker 70 (FIG. 3) in response to a signal transmitted from microprocessor 20 via line 72. LED 66 will light indicating a warning state according to certain predetermined parameters monitored by microprocessor 20. A warning state would indicate that certain operating parameters are being exceeded that could be of concern, but that do not warrant terminating the therapeutic procedure being undertaken. Preferably simultaneously with a lighting of LED 66 and the sounding of the distinctive tone, a message appropriate to the particular warning signal would be displayed in display 22. For example, certain predetermined warning events as shown in Table 1, below, may be programmed to trigger the lighting of LED 66 and the display of the warning message corresponding to the event triggering the warning state. Table 1 is meant to be exemplary only and not limiting of the present invention.

TABLE 1

| Event Triggering Warning State | Monitored Condition | Failure Mode | Action | Warning Message Displayed |
| --- | --- | --- | --- | --- |
| 1. Conductive Fluid Low | Conductive Fluid Volume | Volume = 0 | None | Conductive Fluid Low |
| 2. Impedance Approaching Max/Min Limit | Impedance | Impedance within 25% of the maximum/ minimum limit | None | Impedance approaching limit |

TABLE 1-continued

| Event Triggering Warning State | Monitored Condition | Failure Mode | Action | Warning Message Displayed |
| --- | --- | --- | --- | --- |
| 3. Approaching end of therapy | Time elapsed | 1 minute to end of maximum therapy time | None | 1 minute remaining |

It will be understood that other warning triggering events could also be used to generate a warning message and that the present invention is not limited to those listed here.

When a therapy failure state occurs, LED 66 may light and speaker 70 may sound the distinctive tone appropriate for this state. This state will occur when a therapy session has ended prematurely, for example, as a result of exceeding the maximum impedance. When a therapy failure event occurs, the VETAD 10 will remain functional and a new therapy can be programmed and begun. As with the warning state, a warning message will be displayed in display area 22. For example, certain predetermined warning events as shown in Table 2, below, may be programmed to trigger the lighting of LED 66 and the display of the warning message corresponding to the event triggering the therapy failure state.

TABLE 2

| Event triggering therapy failure state | Monitored Condition | Failure Mode | Action | Warning Message Displayed |
| --- | --- | --- | --- | --- |
| 1. Impedance out of range | Impedance | Above/below the maximum/ minimum impedance | End Therapy | Impedance High/Low |
| 2. Conductive fluid exhausted | Conductive fluid volume | Volume = 0 | End Therapy | Conductive fluid out |
| 3. Arc detected | Presence of an arc | Exceed the predetermined number of allowed arcs | End Therapy | Arc detected |
| 4. Temperature too high | All active thermocouples or thermistor | Temperature exceeds hardwired safety limit | End Therapy | Temperature too high |
| 5. Maximum therapy timer | Time elapsed | Maximum therapy time reached | End Therapy | Maximum therapy time reached |

It will be understood that other therapy failure triggering events could also be used to generate a therapy failure warning message and that the present invention is not limited to those listed here.

When a system failure condition occurs, the system failure LED 66 will be lit, the appropriate tone sounded, and corresponding warning message displayed. For example, certain predetermined warning events as shown in Table 3, below, may be programmed to trigger the lighting of LED 66 and the display of the warning message corresponding to the event triggering the system failure state.

TABLE 3

| Event triggering system failure state | Monitored Condition | Failure Mode | Action | Warning Message Displayed |
|---|---|---|---|---|
| 1. Self test fails | All parameters | Any failure | Inhibit all operation | System failure-maintenance required |
| 2. Software watchdog timer | Watchdog timer | Timer expires | Inhibit all operation | System failure-maintenance required |
| 3. Broken thermocouple | Thermocouple continuity | Open thermocouple | End Therapy | Faulty thermocouple |

It will be understood that other system failure triggering events could also be used to generate a warning message and that the present invention is not limited to those listed here.

Alternatively, where a display such as display 22 is used, the warning condition may be signaled by an appropriate warning light appearing on the display rather than a separate LED.

VETAD 10 may utilize a primary thermocouple in its operation and may utilize one or more secondary thermocouples to monitor the temperature of the tissue being ablated and the surrounding tissue temperature. Thus, the primary thermocouple may be placed within or near the area of desired tissue ablation and the secondary thermocouples may be placed either at the desired perimeter of the lesion to be created or within an area of tissue outside of the tissue to be ablated or both. More generally, the secondary thermocouples will be placed wherever it is desired to measure tissue temperature. With some surgical instruments, the thermocouples may be included with the surgical instrument rather than provided for separately. VETAD 10 and the operation of the pump 16 and generator 18 can therefore be controlled based upon measured temperatures, as will be described further below.

VETAD 10 will also provide an impedance measurement 90 between the virtual electrode and the tissue being treated. As noted, it is desired to maintain the impedance between about ten (10) ohms and about five hundred (500) ohms. Maintaining the impedance within this general range will allow the continuous application of radio frequency power to the patient and thus allow the ablation procedure to continue. Failure to maintain the impedance within this general range will allow the current density or voltage amplitude to increase locally, which may in turn cause steam bubbles to form and desiccation of the tissue, damage to the disposable surgical instrument, the generator 18, or a combination thereof. Desiccation, in turn, may allow arcing between the electrode and the tissue. As the impedance rises, the VETAD 10 will reduce the amount of applied radio frequency power according to predetermined criteria to be discussed below. Generally, the conductive fluid flow rate will not be diminished, however, resulting in the continued flow of fluid away from the surgical instrument. This continued flow recouples the radio frequency energy to the tissue, enlarges the virtual electrode, reduces the current density, and thus reduces the impedance.

VETAD 10 will also preferably include an arc detection circuit 92. In addition to occurring because of the desiccation of tissue mentioned previously, arcs may occur as a result of an air bubble or other failure to deliver an adequate timed flow of the conductive fluid or an inadequate fluid flow rate for the level of radio frequency power applied to the tissue. Thus, as will be described further below, the arc detection circuit 92 will shut off the applied radio frequency power when a predetermined number of arcs are detected within a predetermined time period.

The total ablation time and ablation intervals will also preferably be controlled by VETAD 10. Thus, VETAD 10 may include a clock circuit 120 that communicates with microprocessor 20 over a line 122. It is desirable to control the total ablation time to facilitate patient safety and prevent the application of radio frequency power to the patient beyond that maximum time period. Thus, VETAD 10 will include a clock for recording the total time that ablative radio frequency energy is applied to the patient. When the maximum time limit is achieved, which may be predetermined by the manufacturer and thus not subject to operator control or left to the discretion of the operator to input as a parameter for a particular procedure, VETAD 10 will automatically cease to apply radio frequency power to the patient. If desired in a particular embodiment of the present invention, once the VETAD 10 has reached the maximum ablation time, an ablation interval timer may be activated to prevent beginning anew the application of radio frequency power to the patient. The interval timer will prohibit reactivation of the generator 18 until a predetermined time period has expired, thus allowing the generator 18 to cool and to prevent the continuous, uninterrupted application of power to the patient.

Yet another control function of the VETAD 10 will be to control the pre-ablation infusion of the conductive fluid into the tissue to be ablated. The period of pre-ablation infusion can be either determined by the user or defaulted based upon the particular disposable surgical instrument 26 to be utilized. Pre-ablation infusion will allow the interstitial permeation of the conductive fluid and the creation of the virtual electrode. The pre-ablation infusion period may be shortened from the full period with the same or different rates of infusion where another ablation procedure will be performed with the same instrument placement or may be set to a full pre-infusion period at the full flow rate for new instrument placements.

It will be understood that upon start up of VETAD 10 that certain self checks will be made. Once the ablation therapy procedure is begun, the pre-ablation infusion will begin and extend for a pre-determined time and at a predetermined flow rate. In one embodiment of the present invention, following the pre-ablation infusion, an impedance check will be made by applying a predetermined power level to the tissue and measuring the impedance. If the impedance falls within a predetermined range set by either the operator or the surgical instrument 26, then the ablation procedure will begin. If the impedance does not fall within the predetermined range, the pre-ablation infusion will be continued for a predetermined, extended time period, by way of example, a time period equal to at least twenty percent (20%) of the original pre-ablation infusion time period, and another impedance check will then be taken. This pre-ablation infusion/impedance check cycle will be repeated a predetermined number of times, at least once and preferably three times. If the impedance does not fall within the specified range at the end of the predetermined number of infusion/impedance check cycles, then VETAD 10 will discontinue the ablation procedure.

The VETAD 10 will be operable in either an automatic or auto mode and a manual mode. In automatic mode, control of the ablation procedure and thus of VETAD 10 will advantageously utilize at least one of several methods or control loops including a primary and secondary temperature control loop, impedance control of radio frequency power loop, and impedance control of conductive fluid flow loop. Initially, upon startup of the VETAD 10, the VETAD 10 will be in an automatic mode of operation and will operate according to default parameters and control functions for the temperature thresholds, fluid flow rate, and radio frequency power levels. It should be understood, however, that the disposable surgical instrument 26 may indicate that the apparatus 10 is to operate in a manual mode upon start up. These parameters will be controlled based upon either operator inputted parameters such as tissue type and desired lesion size or upon the recognition by the microprocessor 20 of the particular type of surgical instrument based upon the pin connection or the like between the surgical instrument 26 and the VETAD 10 or upon the default parameters supplied to VETAD 10 by the memory 42 of the instrument 26. When in the automatic mode of operation, the operator of the VETAD 10 will still be able to change certain predetermined operational parameters, including the maximum power level and the time to maintain the predetermined primary and secondary temperatures.

An operator may determine that a manual mode of operation is preferable to the automatic mode of operation. In the manual mode, certain of the control loops, such as the primary temperature control loop, will be disabled and the generator 18 will operate at a constant power output. The impedance control of radio frequency power will remain activated to provide a safety margin for the patient. In addition, the microprocessor 20 will terminate the application of radio frequency power if either the primary or any secondary temperature maximum is exceeded. When in the manual mode of operation the operator will be able to control the radio frequency power level, which shall remain constant unless changed by the operator, the primary and secondary temperature thresholds, the conductive fluid flow rate, the pre-ablation infusion rate, and the pre-ablation infusion time period.

Figure 5:
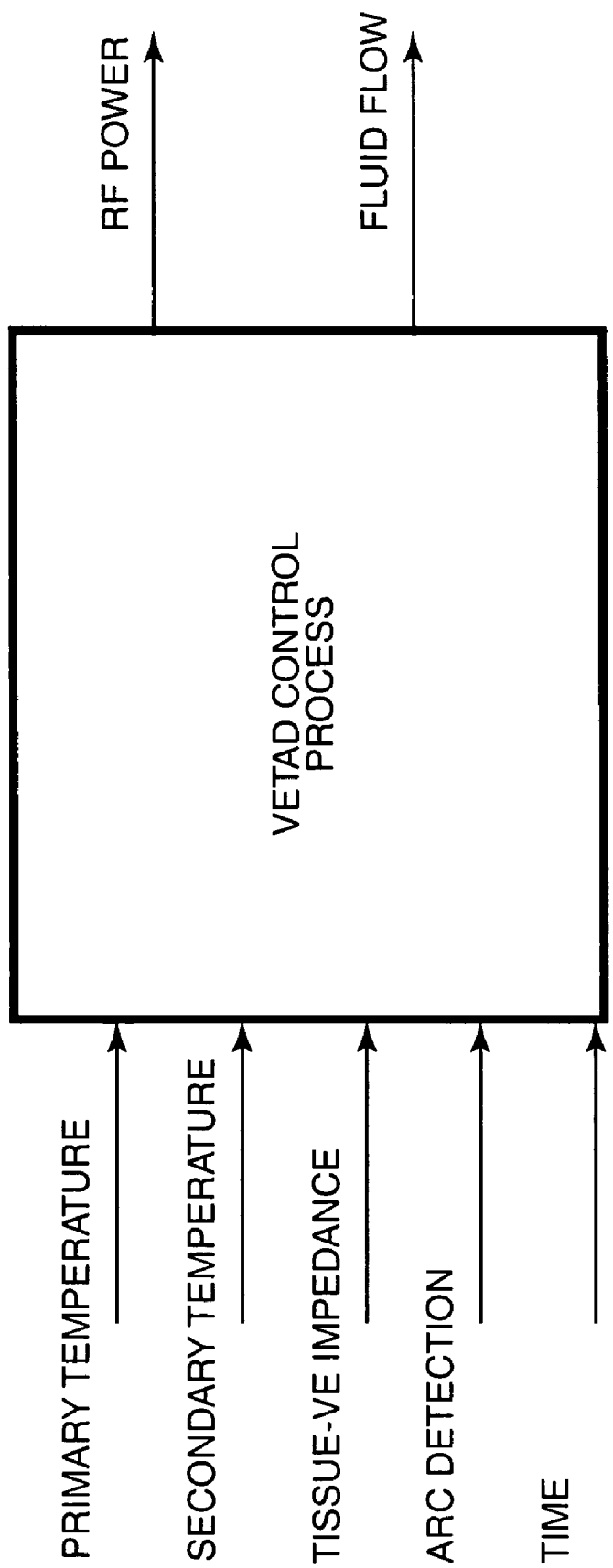
FIG. 5 depicts in general schematic outline the various parameters that may be measured and controlled by the present invention.

To summarize the foregoing, the present invention will provide apparatus and method for therapeutically ablating tissue in response to a variety of measured parameters. Generally, the ablation process must be controlled in response to a variety of parameters due to the variations in the thermodynamic, electrical conductivity, and fluid dynamic characteristics of the tissue being ablated. In response to the various measured parameters, the present invention will control the virtual electrode and thus the ablation process by varying the applied power and fluid flow. Referring to FIG. 5, it can be seen that the input parameters may include the temperature as measured by a primary temperature measuring device, such as a thermocouple, one or more secondary temperatures as measured by a secondary temperature measuring device, the impedance between the virtual electrode and the ground plate, the detection of arcs, and the time of the application of the RF current or power. The control loops provided by the present invention will control the applied power and the conductive fluid flow in response to one or more of those measured parameters.

The various control loops contemplated by FIG. 5 are shown in Table 4 below.

TABLE 4

| Control Loop Name | Controlled Parameter | Inputs |
| --- | --- | --- |
| Temperature Control Loop | RF Power | Primary Temperature Secondary Temperatures Max RF Power Time |
| Impedance Out-of-Range Control Loop | RF Power | Tissue-Virtual Electrode Impedance Time |
| Arc Detection Control Loop | RF Power | Arc Detection (Impedance) Time |
| Fluid Flow Control | Fluid Flow | Impedance |

Figure 6:
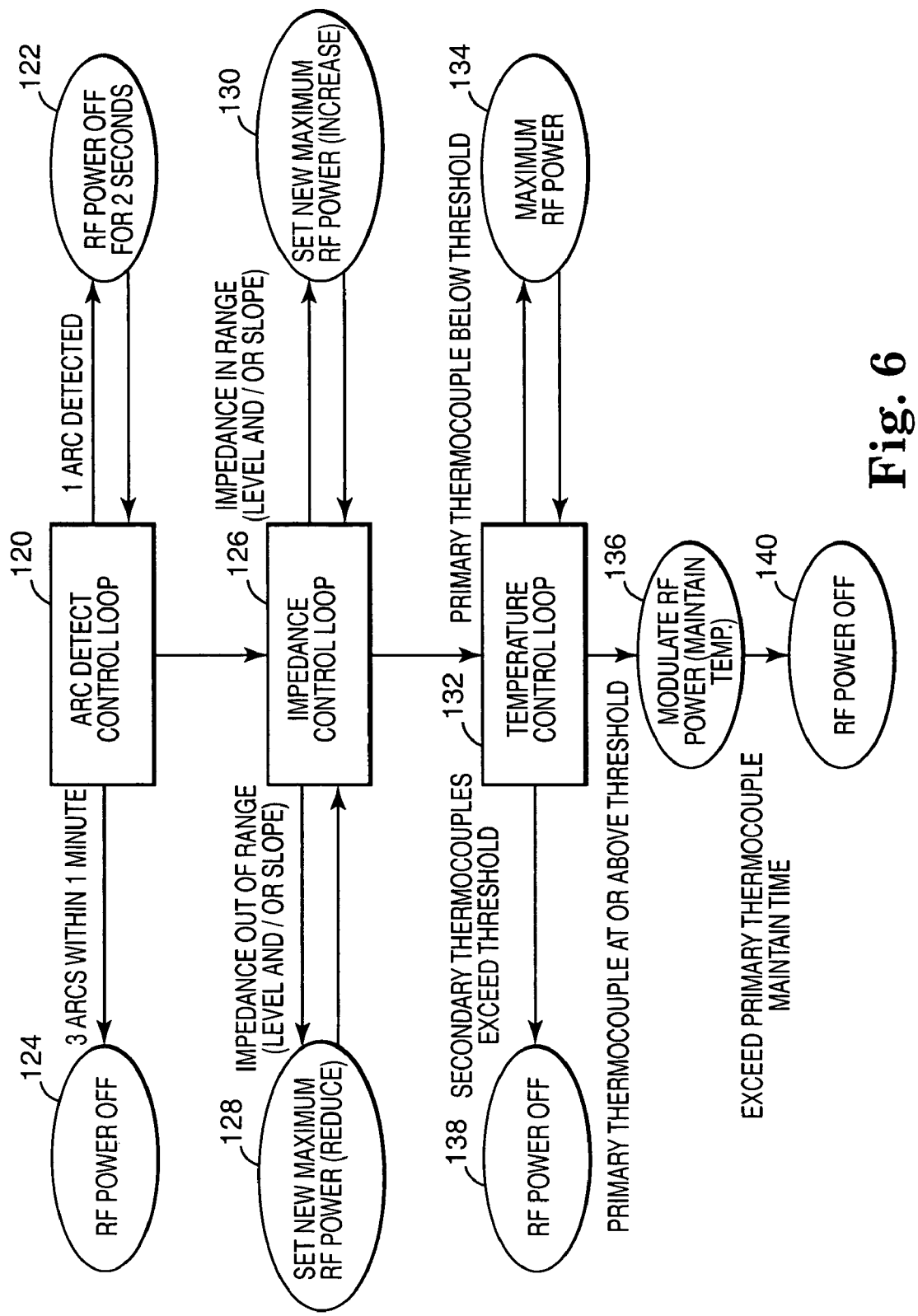
FIG. 6 shows schematically the interaction of the various control loops that may be implemented in accord with the present invention.

As seen in FIG. 5 and Table 4, there are three control loops that function to control the level of applied RF power and one to control the rate of fluid flow. These various control loops will interact with each other to control the ablation process through the present invention. This interaction is shown generally in FIG. 6. The first control loop is the Arc Detection Control Loop 120. An arc can occur if the temperature of the tissue being ablated gets too high and results in desiccation or if an air bubble passes through the surgical instrument into or on the tissue being ablated. This loop will be described in more detail below, but suffice it to say that if an arc is detected the RF current will be discontinued for a predetermined period of time, such as two seconds for example, as at 122 while fluid flow is maintained into or on the tissue. If a predetermined number of arcs are detected in a predetermined time period, such as three or four arcs within one minute, then the ablation procedure will be discontinued as at 114 and an error will be indicated. Preferably, the Arc Detection Control loop will always be running in the background.

Generally, there may be minimum and maximum tissue-virtual electrode impedance values and slope, that is, rate of change, ranges established for each ablation procedure so as to provide for a safe and effective ablation will be established. These values may be established as a default held in the microprocessor 20 in VETAD 10 or the values may be held in memory 42 positioned on the instrument 26, which are subsequently provided to VETAD 10. When the measured impedance is greater that the maximum level of slope established as the threshold then the RF power will be reduced as at 128. Alternatively, if the measured impedance is within the ranges established, then the Impedance Control Loop 126 will increase the applied RF power to a new maximum.

The Arc Detection and Impedance Control Loops are used to monitor the virtual electrode and the ablation procedure and to modify the RF power level if necessary. If such modifications to the applied power lever were not made the virtual electrode may become ineffective at ablating the tissue, thus making the ablation procedure an unsuccessful one. For example, tissue desiccation could occur, thus preventing the RF energy from effectively and safely coupling to the tissue.

When the measured impedance is determined to be within the desired criteria and stable, control of the RF power will default to the Temperature Control Loop 132. The desired impedance criteria may either be a predetermined range of operation, a threshold, a rate of impedance change or the like. The Temperature Control Loop 132 will control the application of RF current to the tissue if the Arc Detect Loop 120 and Impedance Control Loop 126 are satisfied. Preferably, since tissue temperature determines whether cell death occurs, it is desirable for Temperature Control Loop 132 to maintain control of the ablation procedure throughout the entire ablation process. Generally, the Temperature Control Loop 132 will always be monitoring a primary temperature during an ablation procedure and will preferably also be monitoring at least one secondary temperature. The primary temperature will typically be substantially near the center or edge of the lesion to be created while the secondary temperatures will be spaced therefrom at predetermined locations. Once again, maximum values for both the primary and secondary temperatures will be established and held either in memory in VETAD 10 or will be supplied to VETAD 10 and thus the microprocessor by a microchip held on instrument 26. If the primary measured temperature is below the maximum temperature established for the particular ablation procedure, then the RF current will be increased to the maximum as at 134. If the primary measured temperature is above the maximum temperature established for the particular ablation procedure, then the RF current will be appropriately reduced, discontinued or modulated as at 136 and as discussed further below. If the temperatures measured by the secondary measuring devices exceeds the secondary threshold, then the RF power will be shut off as at 138. Finally, the Temperature Control Loop will discontinue the application of RF power when the temperature of the primary thermocouple exceeds the primary thermocouple maintain time (which may be from zero to five minutes, with a typical nominal range of about thirty to about sixty seconds) as at 140. In sum, in the automatic mode of operation the Temperature Control Loop 132 will control the application of the RF current to the tissue based upon the temperature measured by the primary temperature measuring device and, if present, upon the temperature measured by the secondary temperature measuring device.

The primary temperature is intended to be the input which controls the ablation procedure and the resulting lesion size. This temperature may be measured by a thermocouple, which may be placed by hand by the clinician. By way of example only, a physician may dispose the primary thermocouple at the outer edge of a tumor. Once the temperature as measured by this thermocouple reaches a predetermined temperature for a predetermined time period of a sufficient duration to ensure the tumor is fully ablated, the procedure will be discontinued. The application of the RF current via the virtual electrode will result in a temperature gradient expanding outwardly from substantially the center of the virtual electrode. The positioning of the primary thermocouple will use the knowledge of the temperature values and temperature rates of change to set the primary thermocouple threshold and maintenance time to create the desired lesion size. It should be understood that more than one primary temperature sensor could be used in accord with the present invention. For example, where the surgical instrument 26 takes the form of a forceps that is used to resect a selected portion of tissue, such as lung or liver, the instrument 26 will ablate tissue along a preselected path. It may be desired to monitor the temperature at more than one location along this resection path. In such a case, instrument 26 would include a plurality of "primary thermocouples" such that the temperature of the tissue being ablated can be monitored at multiple locations.

In general, the Temperature Control Loop 132 will set the RF power to a maximum allowed level until the Primary Temperature threshold is reached. Once the Primary Temperature threshold is reached, the Temperature Control Loop 132 will modulate the RF power such that the temperature threshold is maintained for the predetermined period of time. The time over which the temperature threshold is maintained is specified either by the disposable table held in the memory chip of the instrument 26 or the physician. After the specified time the RF power is shut off and the ablation procedure is successfully complete. The maximum RF power may be established by the physician, a microchip 42 in the surgical instrument 26, or based upon feedback received from the Impedance Control Loop. Similarly, the Primary Temperature threshold may be set by the physician, by the microprocessor in VETAD 10, or by instrument memory 42 forming part of instrument 26.

The Secondary Temperatures, which may also be measured with thermocouples, may be used by the physician to protect tissues and organs near the ablation/lesion area from reaching damaging temperatures. If any one of the Secondary Thermocouples exceeds a specified threshold, then the RF power will be shut off. Again, the Secondary Thermocouple thresholds can be set by the instrument memory 42 or the physician.

Alternatively, the Secondary Thermocouples may be used to ensure that the outer edges of the desired lesion reach adequate temperatures In this implementation the RF power would not be shut off until all of the desired thermocouples (Primary and Secondary) reach the desired temperature. Additionally, the Secondary Thermocouples can be positioned in the desired lesion area to show the temperature gradients as the temperature expands from the center of the lesion. This information—the temperature gradients—can show both that an adequate lesion has been created or that healthy tissue was protected from being ablated.

Figure 7:
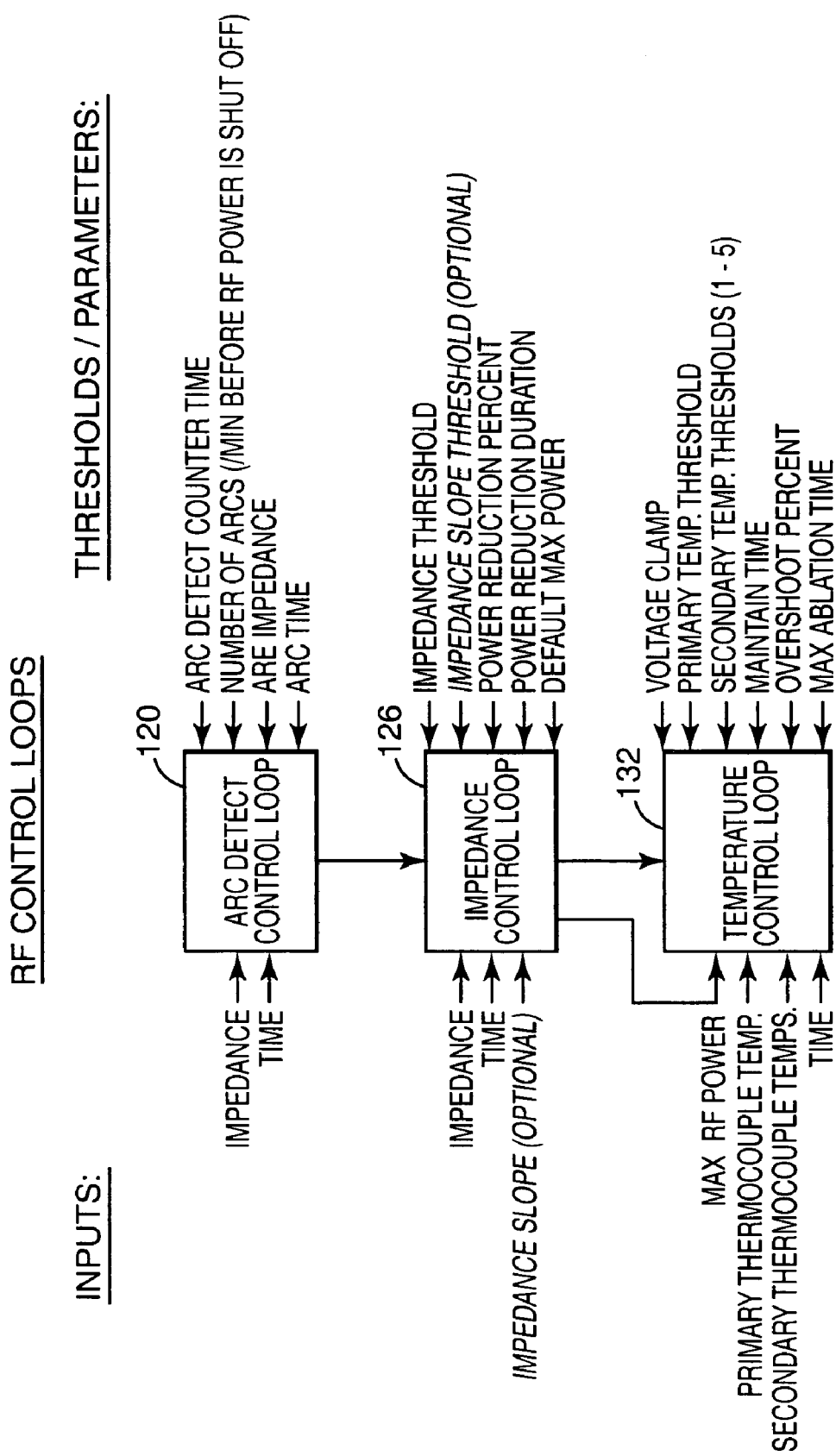
FIG. 7 illustrates the various inputs and parameters used in the control and operation of the RF control loops in accord with the present invention.

Referring now to FIG. 7, the various inputs that can be used to control RF power as well as the various thresholds and parameters can be observed. Thus, for example, the various inputs to the Arc Detection Control Loop 120 will include the impedance measurements and time. These measurements will be compared with parameters that include a counter, total number of arcs counted, the measured impedance of an arc, and the time frame during which successive arcs occur. The inputs to the Impedance Control Loop 126 will include the impedance measurements and time, and if desired, the rate of change in the impedance. These measurements will be compared to the impedance threshold and if desired a rate of change threshold. The control loop will then operate to control the apparatus 10 by varying the applied power in response to parameters such as a power reduction percentage, time during which power is reduced, and the default maximum power for the procedure. The Temperature Control Loop 132 may include as inputs the maximum power, the temperature measurements provided by the primary and secondary thermocouples, and the time. These inputs will be utilized by the control loop 132 and compared against the voltage clamp level, the thresholds for the temperature measurements, the time for which the temperature measurements should be maintained to assure the desired cell death, the temperature overshoot above the threshold allowed before shutdown occurs, and the maximum ablation time. It will be understood that the foregoing inputs, thresholds, and parameters are by way of example and that other inputs, thresholds, and parameters can be utilized with the present invention.

Figure 8:
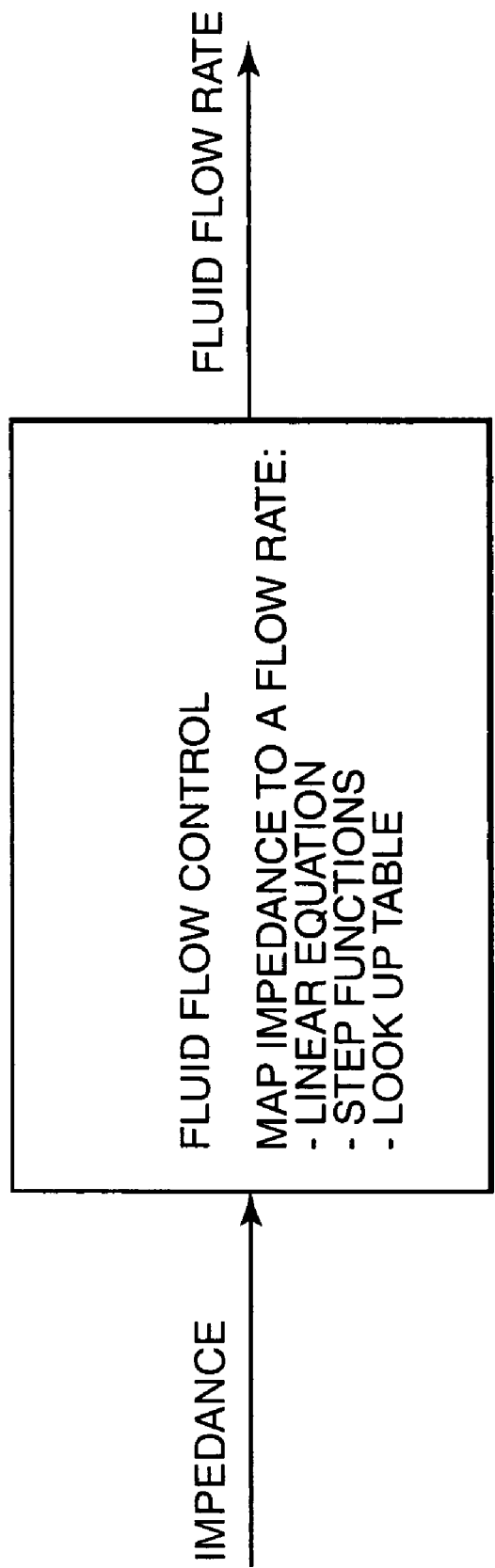
FIG. 8 depicts generally the Fluid Flow Control Loop and the inputs and outputs used in the control of the flow of conductive fluid.

The Fluid Flow Control Loop 150 is shown generally in FIG. 8. Fluid Flow Control Loop 150 may utilize impedance measurements to modify the fluid flow rate. Thus, where the impedance measurement is trending upwardly at an excessive rate or reaches a predetermined level, the fluid flow can be increased to increase the size of the virtual electrode and thus spread the applied power throughout an increased volume of tissue. The increased size of the virtual electrode decreases the current or energy density and thus reduces impedance. The fluid flow rate can be controlled in several ways, such as linearly increasing the fluid flow in response to the measured impedance, providing a step wise change in the fluid flow in response to the measured impedance, or providing a look-up table that provides the desired rate of fluid flow in response to the measured impedance. Generally, the surgical instrument will provide several default parameters to the VETAD 10, such as the default fluid flow rate, the impedance at the default fluid flow rate, the rate of change in impedance to the change in impedance flow rate—the slope—, the maximum fluid flow rate, and the minimum fluid flow rate.

Figure 21:
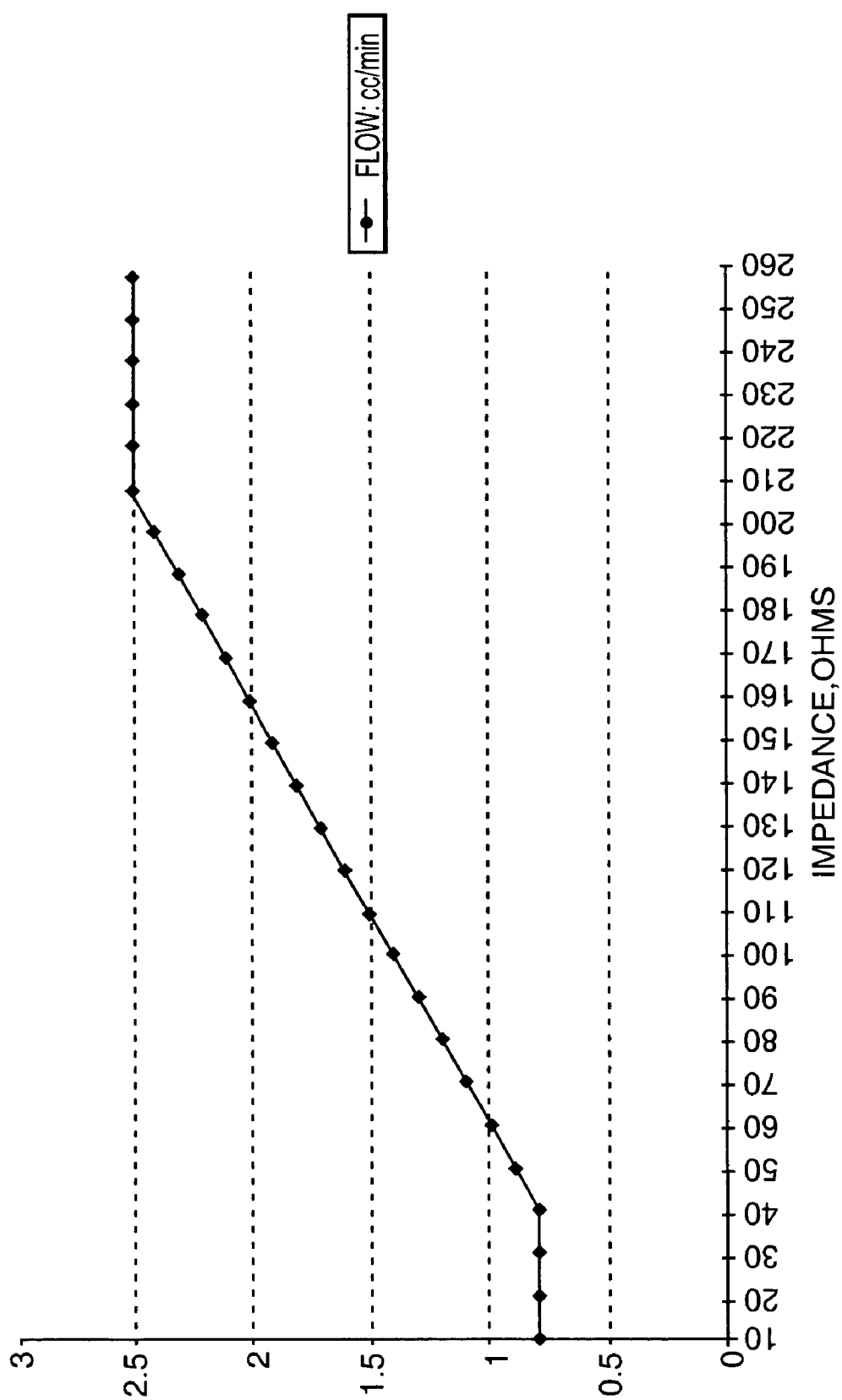
FIG. 21 is a graph showing an example of a fluid flow control function useful in accord with the present invention.

By way of example only, with a linear relationship established between the impedance and the rate of fluid flow, the default fluid flow rate could be set at 1.4 cubic centimeters per minute; the impedance at the default fluid flow rate at 100 ohms; the change in impedance to change in fluid flow rate at 0.1 cubic centimeter per minute per 10 ohms change in impedance; the maximum fluid flow rate at 2.5 cubic centimeters per minute; and the minimum fluid flow rate at 0.8 cubic centimeters per minute. Thus, the flow rate would initially be established at 1.4 cubic centimeters for a default impedance of 100 ohms. For each change in impedance of ten ohms then the flow rate would be correspondingly increased or decrease until the maximum or minimum fluid flow was reached. Such a linear relationship as just described can be graphed as shown below in FIG. 21. Again, it will be understood that this example is exemplary only.

Figure 22:
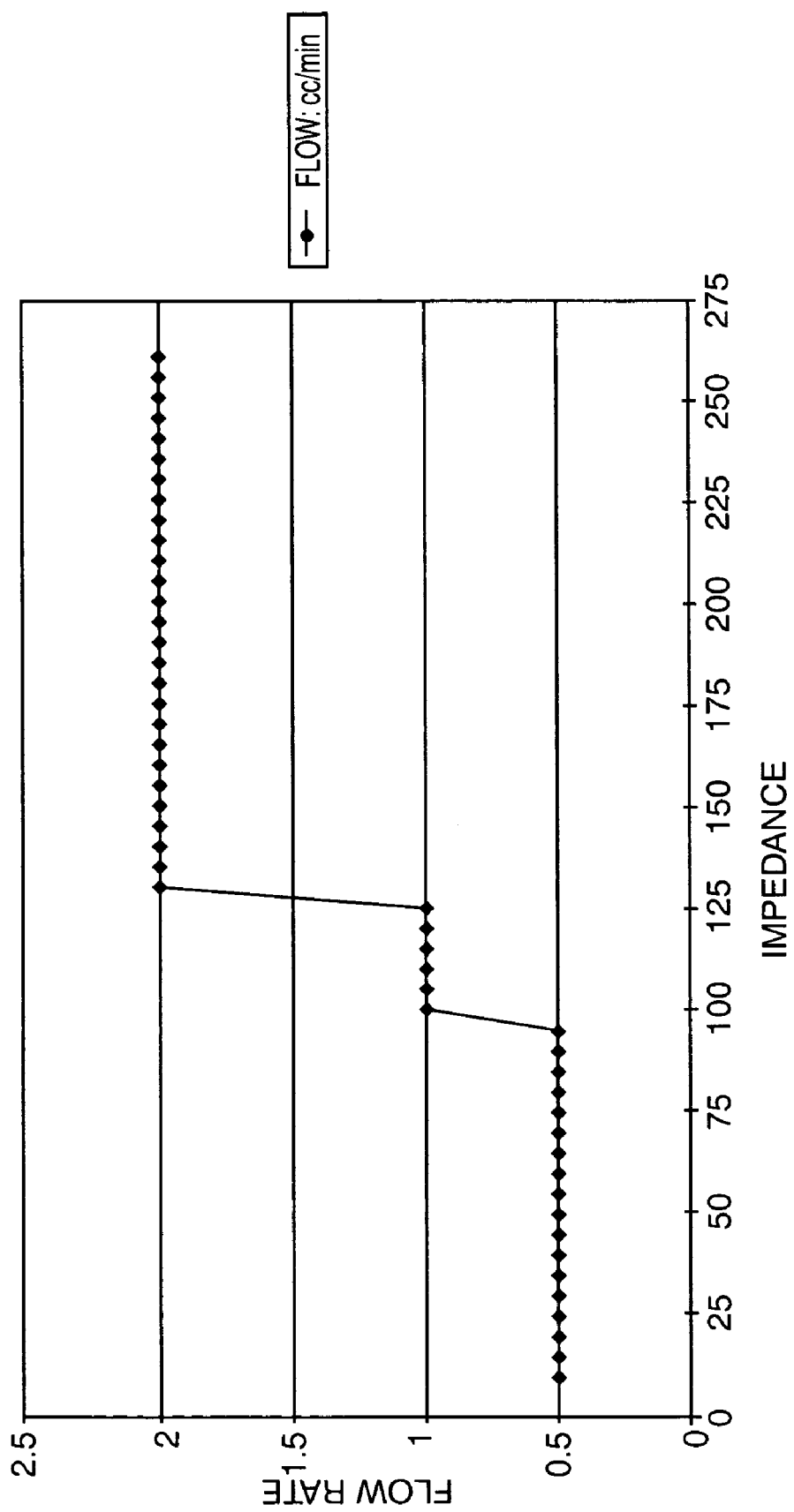
FIG. 22 is a graph showing another example of a fluid flow control function useful in accord with the present invention.

FIG. 22 below illustrates by way of example only a step wise approach to controlling fluid flow based upon impedance measurements. Generally, such an approach may define initial parameters including: nominal fluid flow rate of 0.5 cubic centimeters per minute, a medium fluid flow rate of 1.0 cubic centimeters per minute, a high fluid flow rate of 2.0 cubic centimeters per minute, a medium impedance threshold of 100 ohms and a high impedance threshold of 125 ohms. Generally a fluid flow rate will be established for impedance measurements below a first level and a second fluid flow rate will be established for impedance measurements above the first level. Additionally fluid flow rates can be set for additional impedance measurements. Thus, in the example given and shown below, three flow rates are established based upon the measured impedance as compared with the fluid flow impedance thresholds. Operationally, fluid flow rates should be maintained for a predetermined period of time, such as about one second to about five seconds, before decreasing the flow rate due to a subsequent impedance measurement.

As noted above, flow rate could also be controlled based upon a variety of parameters, including impedance, temperature, and RF power level. Quadratic or higher order equations could be devised to control the flow rate that would increase or decrease the flow rate as desired and at the rate desired.

Figure 9:
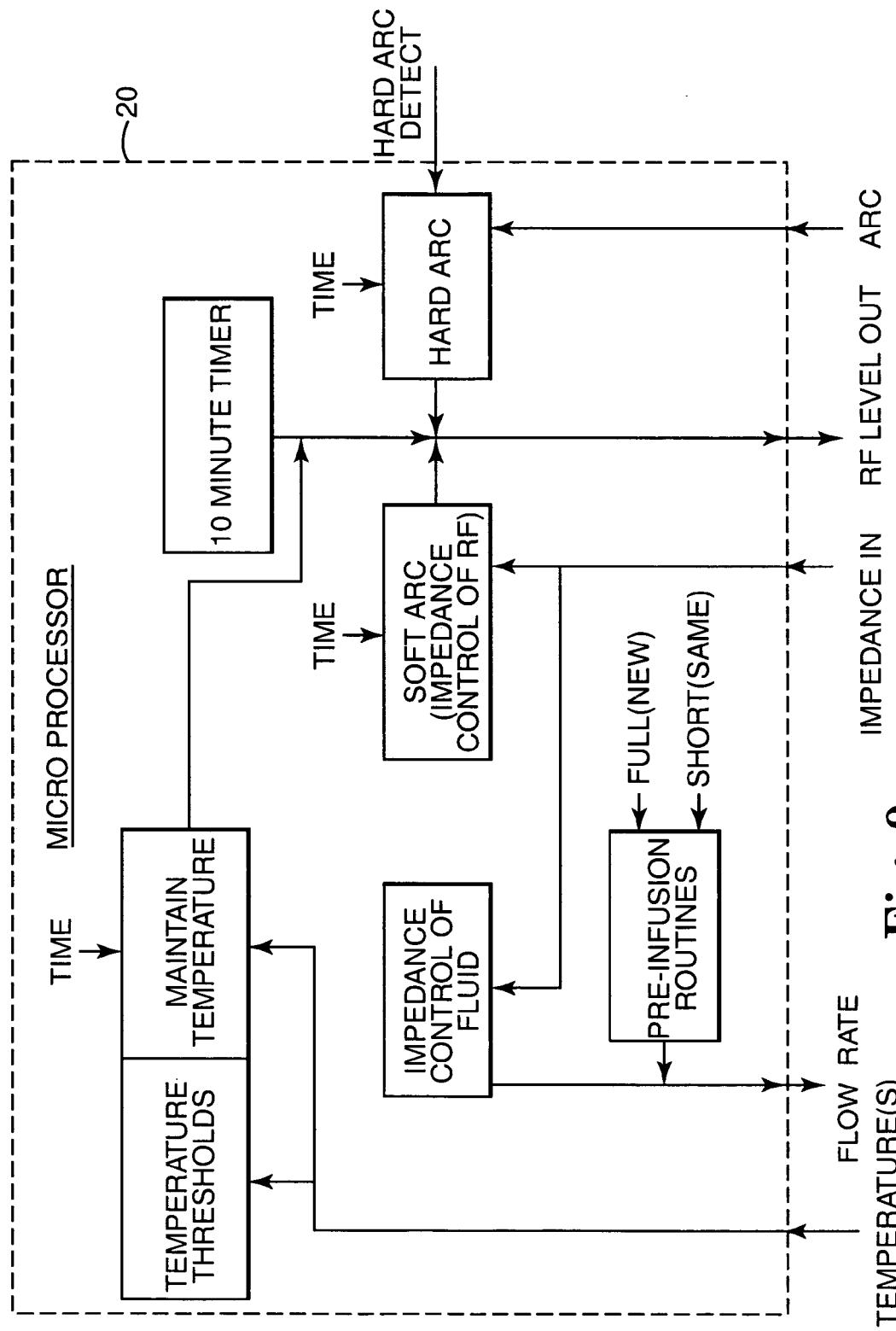
FIG. 9 schematically illustrates the software blocks contained within the microprocessor shown in FIG. 3.

FIG. 9 illustrates the microprocessor 20 and its function generally. Microprocessor 20 will receive as inputs the various temperature measurements, the measured impedances, and detected arcs. It will output signals to control the flow rate and the RF power. Signals indicative of temperature will be compared against temperature thresholds and when the primary temperature reaches the maximum temperature to a temperature maintain timer to monitor the length of time at which the tissue being ablated is held at the maintenance temperature. This information will also be provided to a timer control loop, illustrated as being a ten minute timer for purposes of illustration. The measured impedances will be provided as a signal input into the fluid flow control loop and the soft arc control loop. The fluid flow control loop—the impedance control of fluid—will provide a flow rate to the pump 16 as an output of the microprocessor 20. In addition, inputs will determine whether the initiation of RF power is a new placement or a restart with the surgical instrument 26 at the same site. Where a new placement is made, the pre-ablation infusion rate will be for the full specified time period whereas when the initiation is a restart, a shorter period of infusion will be used.

As noted, the impedance measurement signals will be provided to the microprocessor 20 and processed by the soft arc—the impedance control of RF power—loop. Another input to that loop will be time. When an arc is detected the RF power will be discontinued for a predetermined period of time. Detected arc signals will be provided to the "hard arc" loop which will determine whether the predetermined number of arcs occur within the predetermined time period. If so, the RF power will be discontinued. In addition, a timer which determines how long RF power has been applied will discontinue the application of power upon the expiration of a predetermined time period, such as ten minutes for example.

Figure 10:
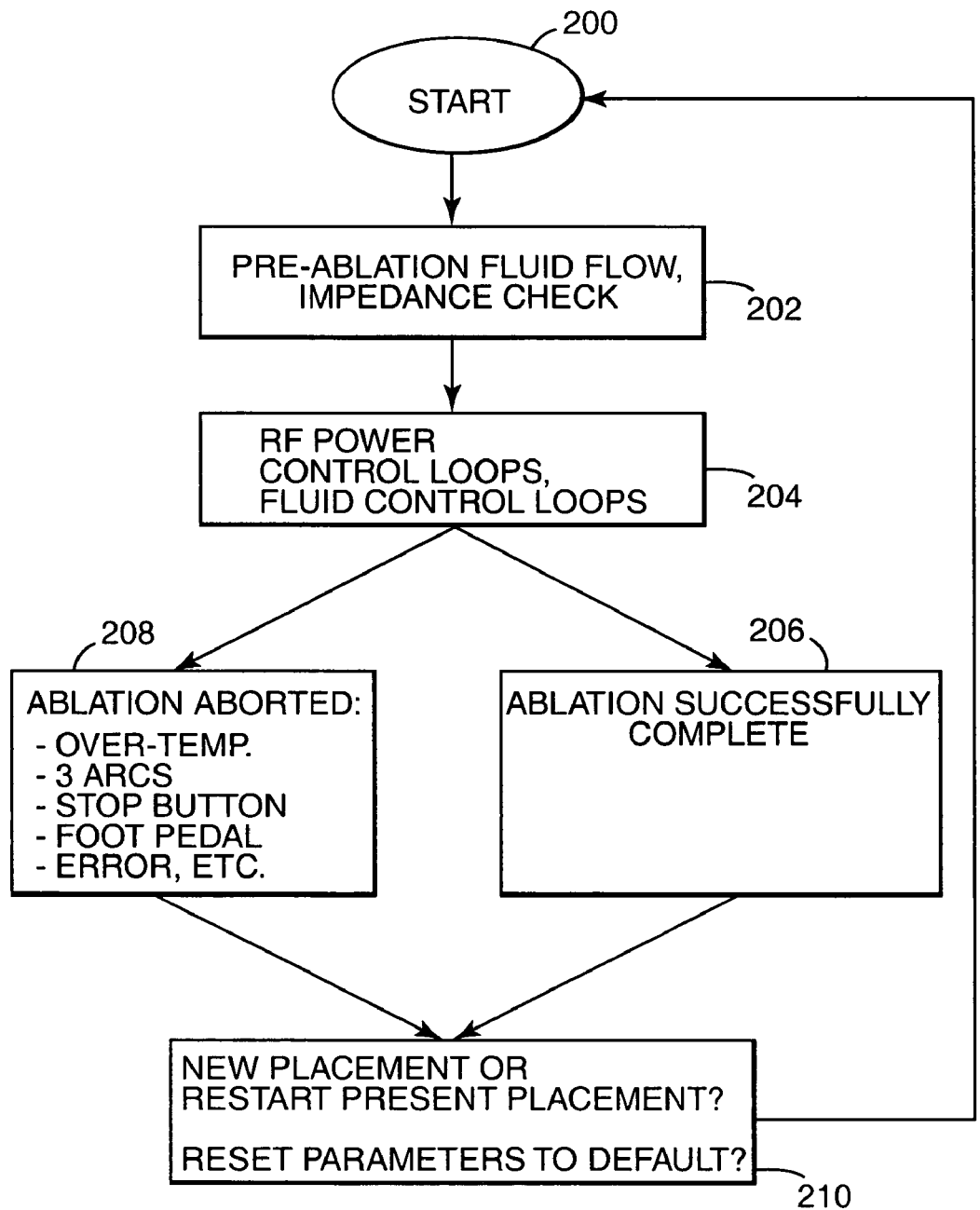
FIG. 10 illustrates schematically the operation of an apparatus in accord with the present invention.

The various control functions of the VETAD 10 having been generally described above, specific details of the operation of the apparatus 10 and the control methods or loops will be discussed below with reference to the figures. Referring to FIG. 10, the overall operation of the apparatus 10 will first be described generally. Thus, following placement of the power source at the site of the desired ablation, at the start of the apparatus 10 as indicated at 200 a pre-ablation infusion of conductive fluid may be made and an impedance check at low power duration, say one watt-second, may be made as indicated at 202. If the impedance check is satisfactory, meaning that the measured impedance is within the predetermined limits of about 10 ohms to about 500 ohms, or some other threshold provided to the VETAD 10 by the instrument 26 or the operator, then the ablation procedure will begin and will be controlled by the various described control loops as at 204. The impedance checks may also look at the difference between the initial impedance measurement and subsequent re-checks of it.

The ablation procedure will then either be successfully completed as at 206 or will be halted for a predetermined reason, such as by exceeding maximum secondary temperature limits or detection of a predetermined number of arcs as indicated at 208. In addition, the ablation procedure can be discontinued manually by use of the stop button 54 on the apparatus 10 or the foot pedal 62. Even where the operating parameters have been determined by the surgeon, the control loops will operate to halt the procedure when certain critical parameters, such as low impedance or high impedance are reached. For example, a low impedance shut off is desirable since the lower the impedance the greater the current that is being routed from the apparatus 10 through the patient and back to the apparatus 10, thereby jeopardizing the electronics of the apparatus 10 and the surgical instrument 26. Alternatively, a high impedance shut down is desirable since that indicates that the tissue closely adjacent the power delivery electrode is desiccating and thus interfering with the distribution of applied power throughout the extent of the virtual electrode. Following either the discontinuation of an ablation procedure or the successful completion of a procedure, the ablation procedure may be restarted or the instrument 26 may be placed anew at another location as indicated at 210 and the procedure started anew. Where a restart occurs, that is, with the same needle placement, the pre-infusion of electrolytic fluid may be selected for the full time at the full flow rate or a reduced time and or a reduced flow rate. The reduced time and flow rate would reduce the likelihood of an occurrence of an excessive fluid delivery to the tissue.

Figure 11:
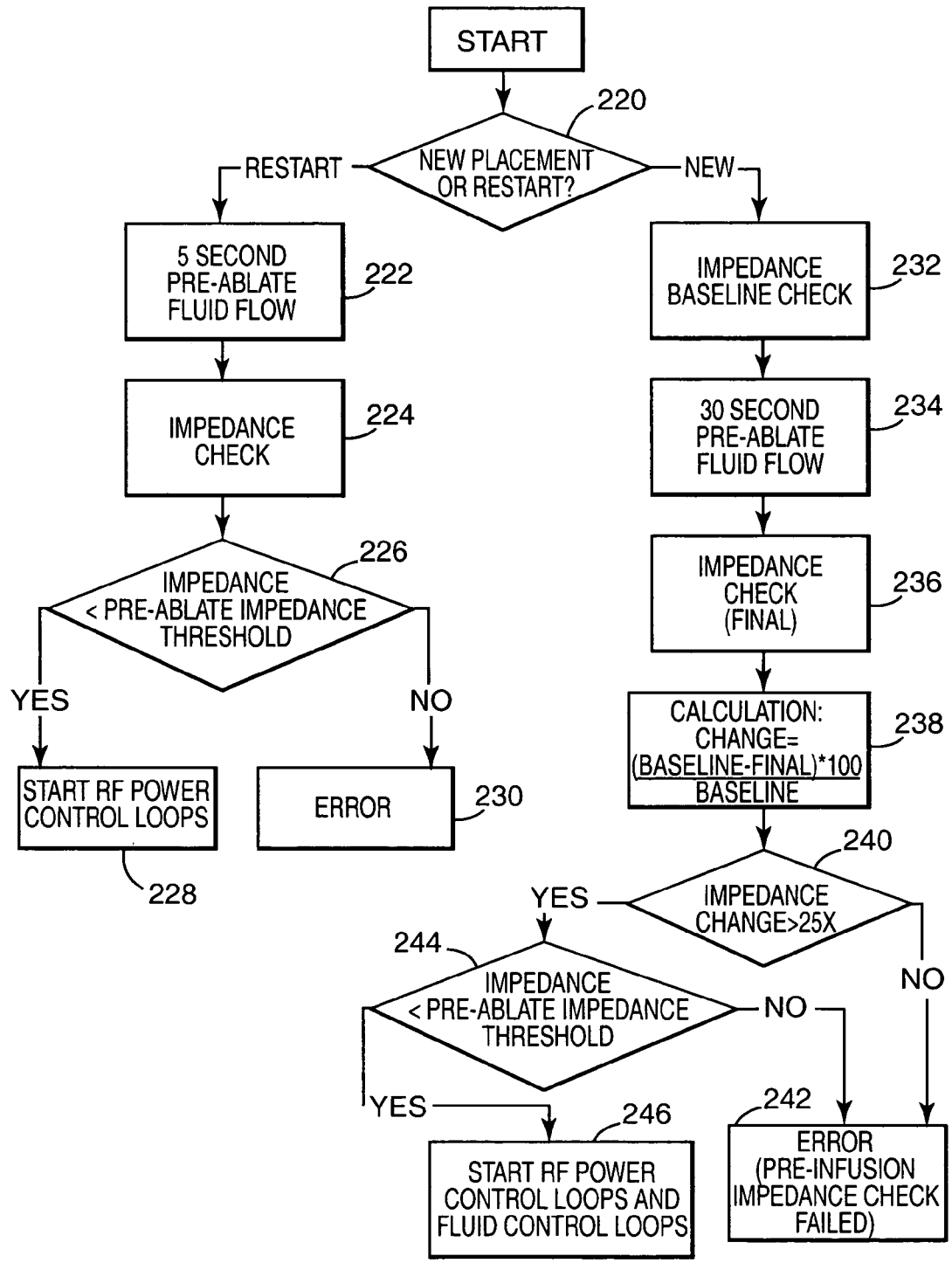
FIG. 11 illustrates a pre-ablation operating routine of an apparatus in accord with the present invention.

Referring now to FIG. 11, a start-up operating routine will be described in greater detail. Thus, at the start of the procedure, it will be determined whether the procedure is a restart at an existing placement or a new placement as at 220. Where a restart is indicated, fluid flow will be preferably initiated for a predetermined period of time, which can be anywhere from about one second to about sixty seconds, as indicated at 222. An impedance check will be made at low power duration, such as about one watt-second but generally 15 watt-seconds or less, as indicated at 224, to determine the initial impedance levels. The impedance check could be made at full power levels, however. The measured impedance will then be compared with a threshold impedance level at 226. If the measured impedance level is below a predetermined threshold, then the RF power control loops will be initiated and the ablation procedure will start, as at 228. If the threshold is exceeded however, then an error will be indicated as at 230 and the procedure will be halted.

Where the start up is for a new placement, that is, a new site for an ablation, a baseline check will be made to initially check the impedance as at 232. Once again, the power level utilized to make this initial impedance check should be minimized to minimize the risk of arcing. Fluid flow will then be initiated for a predetermined period of time and rate as provided by the instrument 26 (or the operator when working in manual mode) as at 234. Once the predetermined time period has elapsed, another impedance check will be made as at 236. A calculation will be performed to determine the percentage change in the impedance at 238. Thus, the impedance measured at 236 will be subtracted from that measured at 232, the product will be divided from the initial baseline measurement and then multiplied by 100 to provide a percentage indication of the impedance change following fluid flow at 234. The percentage change will then be compared to a pre-determined level, such as 25% as indicated in the FIG. 11 at 240. Where the impedance change is less than the threshold, then an error will be indicated as at 242 and the procedure will be halted. If the percentage change is greater than the predetermined percentage change amount, then the measured impedance will be compared with the predetermined, pre-ablation threshold as at 244. If the impedance measurement is less than the pre-ablation impedance threshold then the RF power will be started and the various control loops will be operational as at 246. Where the final impedance measured at 236 is greater than the threshold impedance level at 244 the procedure will be halted an error signal will be given as at 242.

The routine illustrated in FIG. 11 is intended to safeguard both the patient and the apparatus 10. Where the impedance checks indicate that the impedance is too high, that is above the threshold, then the risk of arcing increases. Finally, where the impedance fails to drop by a predetermined percentage, then there is an indication that the initial flow of conductive fluid has failed to sufficiently disperse within or upon the tissue to provide for a safe ablation of the desired tissue. The aforementioned predetermined percentage may be in the range of 0% to 100% of the initial impedance measurement. Setting the predetermined percentage to 0% has the effect of disabling the feature.

Table 5 provides an example of the various parameters that can be utilized to control the apparatus 10 in a pre-infusion routine similar to that illustrated in FIG. 11 and the typical values associated with those parameters.

TABLE 5

| PARAMETER | TYPICAL VALUE | LOCATION | DESCRIPTION |
|---|---|---|---|
| Flow Rate | 0.5 cc/min | Surgical Instrument | Flow rate for pre-ablate infusion. If zero, then skip pre-ablate infusion |
| Pre-ablation Time for New Placement (Full Pre-ablation infusion) | 30 sec | Surgical Instrument | Length of time for initial pre-ablate infusion |
| Pre-ablate Impedance Change | 25% | Surgical Instrument | Minimum amount impedance must fall from pre-infusion baseline to post infusion measurement for ablation to continue |
| Pre-ablate Impedance Threshold | 75 ohms | Surgical Instrument | If impedance below threshold, start ablation with out regard to success of Pre-ablate Impedance Change |
| Restart Pre-ablation Flow Time for Same Placements (Short Pre-ablation infusion) | 5 sec | Surgical Instrument/ Table in memory | Time to infuse before RF On in case of restarted or continued ablation |

Figure 12:
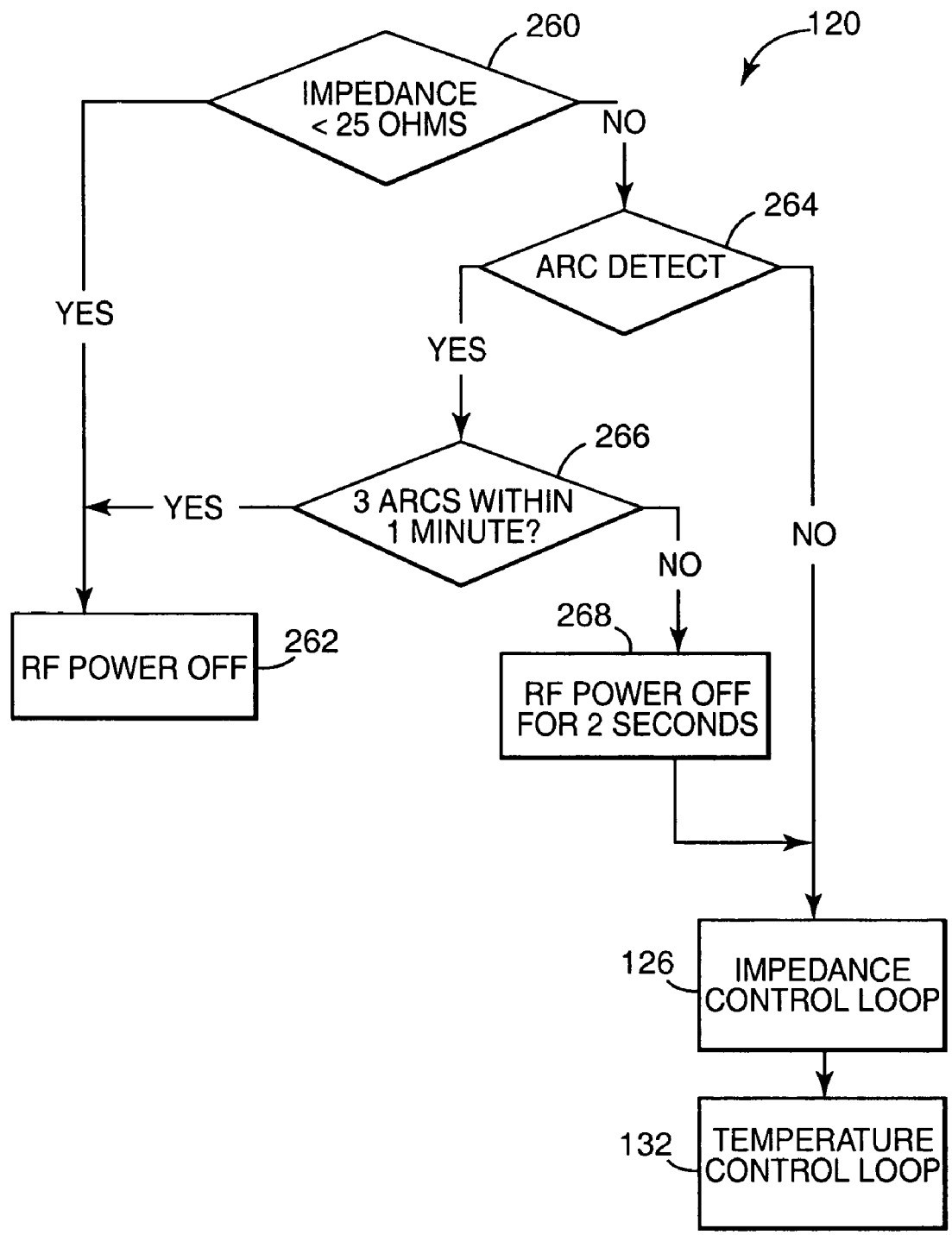
FIG. 12 illustrates an arc detection loop of an apparatus in accord with the present invention.

Referring now to FIG. 12, the Arc Detection Loop 120 will be explained more fully. The impedance measurements provided by apparatus 10 will be compared with a minimum impedance threshold at 260. As illustrated, the minimum has been indicated at 25 ohms. This minimum could be set higher or lower as desired. Low impedance measurements indicate, however, that the power generated by RF generator 18 contains high current levels. Consequently, to avoid damage to the apparatus 10 and the instrument 26, when the measured impedance falls below the minimum, the power will be shut off as indicated at 262.

If the impedance measurements exceed the minimum level, the Loop 120 will monitor the impedance measurements to determine whether arcing is occurring at 264. Arcing is indicated by high impedance measurements. For purposes of illustration, an arc is defined as an impedance measurement exceeding a predetermined level, for a predetermined period of time, here, 500 ohms for 500 milliseconds. Within the limits of the electronics, shorter or lesser time periods can be defined for the arc detection. If an arc meeting the predetermined criteria is detected, then the total number of arcs will be determined. When the total number of arcs exceeds a predetermined number within a predetermined time period as at 266, then the power will be shut off as at 262. As illustrated, three arcs occurring within a minute will result in power being shut off and the procedure discontinued. It should be understood that a different number of arcs, such as two, four, or some greater number could also be used consistent with patient safety and the safe operation of the apparatus 10. If an arc is detected, but the criteria for a complete shut down of power is not met, the power will be shut off for a predetermined period of time, here two seconds as at 268. Fluid flow will be continued during this time period, allowing the conductive fluid to spread throughout the desired tissue ablation site. After two seconds, or such other period as is specified, power will again be applied to the patient through the virtual electrode. Where the Temperature Control Loop is maintaining temperature or where the generator is being operated manually, then a certain amount of time will be added to the maintain time timer to make up for the period of time over which the RF power was off. Where an arc is not detected then control of the ablation procedure and thus the RF power will be turned over to first the Impedance Control Loop 126 and then the Temperature Control Loop 132. It should be noted that these control loops could operate simultaneously, but in the order of precedence shown in FIG. 7. That is, each control loop could operate at all times, with control precedence of the applied RF power and fluid flow being In addition, after a power shut off as at 268, control will be turned over to first the Impedance Control Loop 126 and then the Temperature Control Loop 132.

Table 6 below indicates the various parameters and typical value that can be utilized by the Arc Control Loop 120. It will be understood that these parameter values can take on other values and that the present invention is not limited to these parameters.

detect and count the number of arcs that occur. If a predetermined number of arcs, say three, occurs within a predetermined time limit, say one minute, then the radio frequency power will be turned off, Thus, VETAD 10 will detect arcs as at 302, count the number of arcs occurring within a time period $\Delta T$ as at 304, and compare the number detected at 306 with the allowed maximum number of arcs occurring within a predefined time interval held in memory as at 308. If the maximum limit is exceeded, then the therapy will terminate as at 310. If, however, the maximum is not exceeded, then the RF power will be discontinued for a predetermined period of time as at 312. Where control of the ablation process requires that the temperature be maintained for a predetermined period of time, then a predetermined number of seconds will be added to that time to take into account of heat dissipation during the power off interval. As shown in the FIG., and by way of example, a power shutdown due to the occurrence of an arc may be two seconds as at 312 and four seconds may be added to the maintain temperature timer as at 314. In any event, therapy will continue.

Alternatively, the maximum number of arcs allowed $\text{Arc}_{mxax}$ 308 could be a predetermined threshold average rate of arc occurrence. Microprocessor 20 would then determine the average rate of arc occurrence and compare it with $\text{Arc}_{mxax}$ at 306. When the average rate exceeded the threshold average rate, say for example, one arc per 15 seconds or one arc per twenty seconds, then the therapy would end as at 310.

Figure 14:
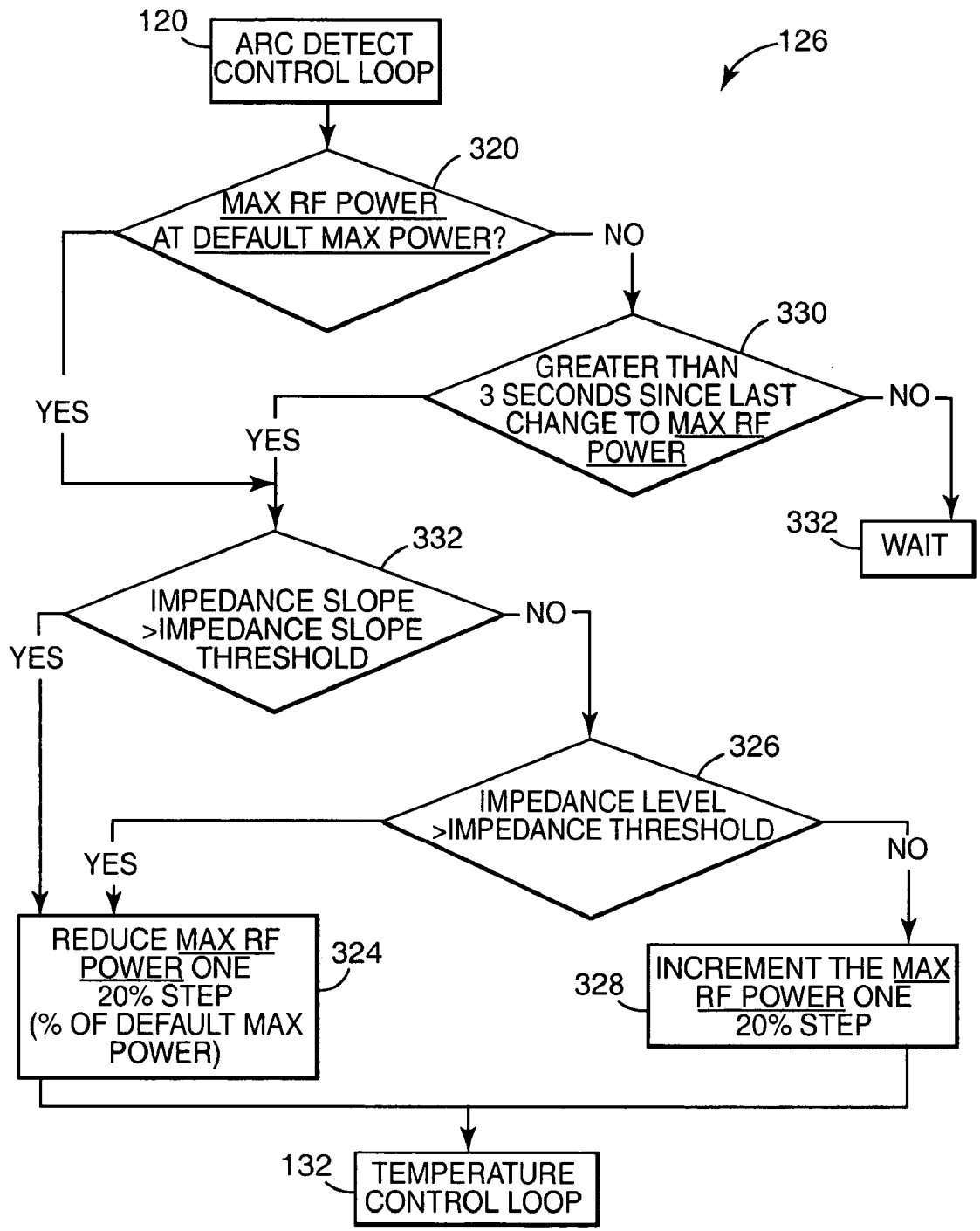
FIG. 14 illustrates an impedance control loop of an apparatus in accord with the present invention.

Referring now to FIG. 14, the Impedance Control Loop 126 will be described. This loop along with Temperature Control Loop 132 provides the primary control, that is RF power modulation, of the ablation procedure, unlike the Arc Detection Loop 120, which functions primarily to simply turn the power off when certain conditions, such as an arc detection, occurs. Thus, as the power is turned on, the applied power will be compared as at 319 against the default maximum power level for the procedure, which as previously noted may be set by the surgeon or by the disposable instrument 26. When the applied power is compared to the default maximum power at 319 and found to be below the maximum for the procedure, the period of time that has elapsed since the last power increase or decrease will be determined as at 320. It is desirable to wait a predetermined

TABLE 6

| PARAMETER | TYPICAL VALUE | LOCATION | DESCRIPTION |
|---|---|---|---|
| Number of Arcs | 3 | Table | No. of arcs before ablation ends (over Arc Detect Counter Time) |
| Arc Impedance | 500 ohms | Table/HardWare | Impedance threshold at which arc is declared |
| Time for Arc | 500 msec | Table/HardWare | Max time period in which arc must be detected |
| Arc Detect Counter Time | 1 minute | Table | Period over which arcs are to be counted towards "Number of Arcs" limit |
| Arc Detect RF Off Time | 2 sec | Table | Length of time RF power is off after arc detected |
| Impedance Low Threshold | 25 ohms | Table/Surgical Instrument | Minimum impedance threshold lower than this and ablation ends |

Figure 13:
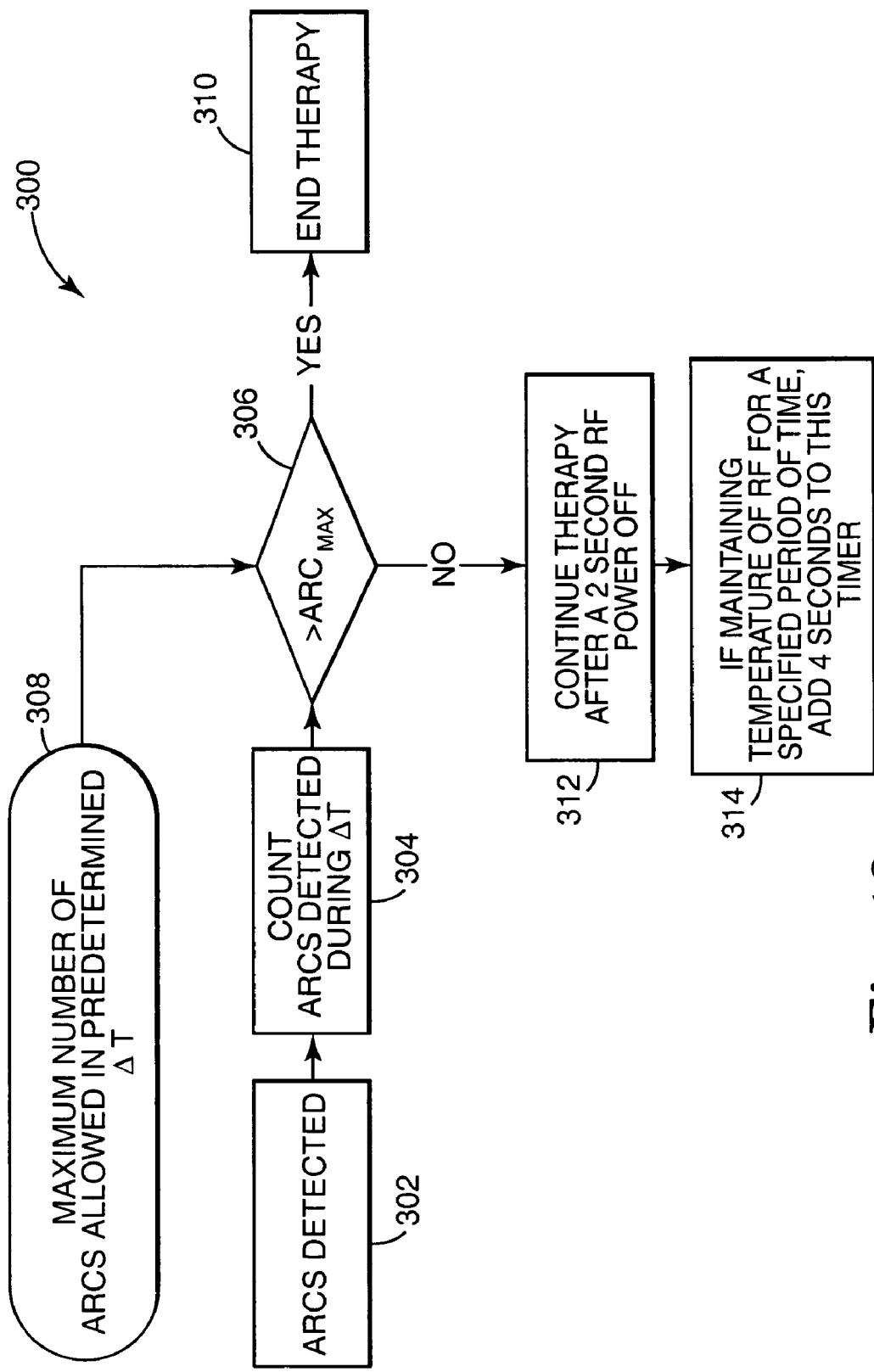
FIG. 13 illustrates a method in accord with the present invention for controlling the application of radio frequency power to a patient based upon detected electrical arcing.

Referring now to FIG. 13, an arc detection control loop 300 will now be shown as described. Thus, loop 300 will period of time between power level increases or decreases to allow the tissue impedance to be evaluated at the present RF power setting. This time constant is chosen based upon the virtual electrode response time, that is, the length of time between the change in a parameter, here power, and the time at which a change is seen in the virtual electrode. Where the predetermined time limit has not elapsed since the last power level increase, then the loop will enter a wait state at 321 until such time limit elapses.

If the applied power is at the default maximum, then the impedance slope, that is, the rate of change of the impedance, will be compared with the impedance slope threshold as at 322. In addition, if the predetermined period of time between allowed changes in Max RF Power has elapsed has elapsed, here, three seconds for purposes of illustration, then the impedance slope comparison of 322 will be conducted. If the impedance slope is greater than the slope threshold, the maximum RF power, which is the maximum power allowed based upon the measured impedance, will be reduced a predetermined amount, say twenty percent for example, which is a predetermined percentage of the default maximum power at 324.

If the measured impedance slope is less than the slope threshold, then the impedance will be compared with the impedance threshold as at 326. If the measured impedance is greater than the impedance threshold, then the maximum RF power will be reduced as at 324. If the measured impedance is less than the impedance threshold, then the maximum RF power will be incremented a predetermined percentage of the default maximum power as at 328. Control over the ablation process will then pass to the temperature control loop 132. The level of increments and decrements in the applied power can vary; for purposes of illustration a twenty percent increment/decrement percentage of the default maximum RF power has been selected.

Table 7 below indicates the parameters and values that may be used with the Loop 126.

TABLE 7

| PARAMETER | TYPICAL VALUE | LOCATION | DESCRIPTION |
|---|---|---|---|
| Default Max Power | 100 watts | Surgical Instrument | Maximum power which generator can use in an ablation |
| Power Reduction Duration | 3 sec | Surgical Instrument | Time between changes in RF output due to impedance/soft arc detect |
| Impedance Threshold (Soft Arc) | 200 ohms | Surgical Instrument | Upper impedance threshold values > will result in power reductions |
| Soft Arc Impedance Slope | 5 ohms/sec | Surgical Instrument | |
| Power Reduction Percent | 20% | Surgical Instrument | Upon detection of soft arc, power is reduced by this much at each step. Percentage of Default Max Power. |

Figure 15:
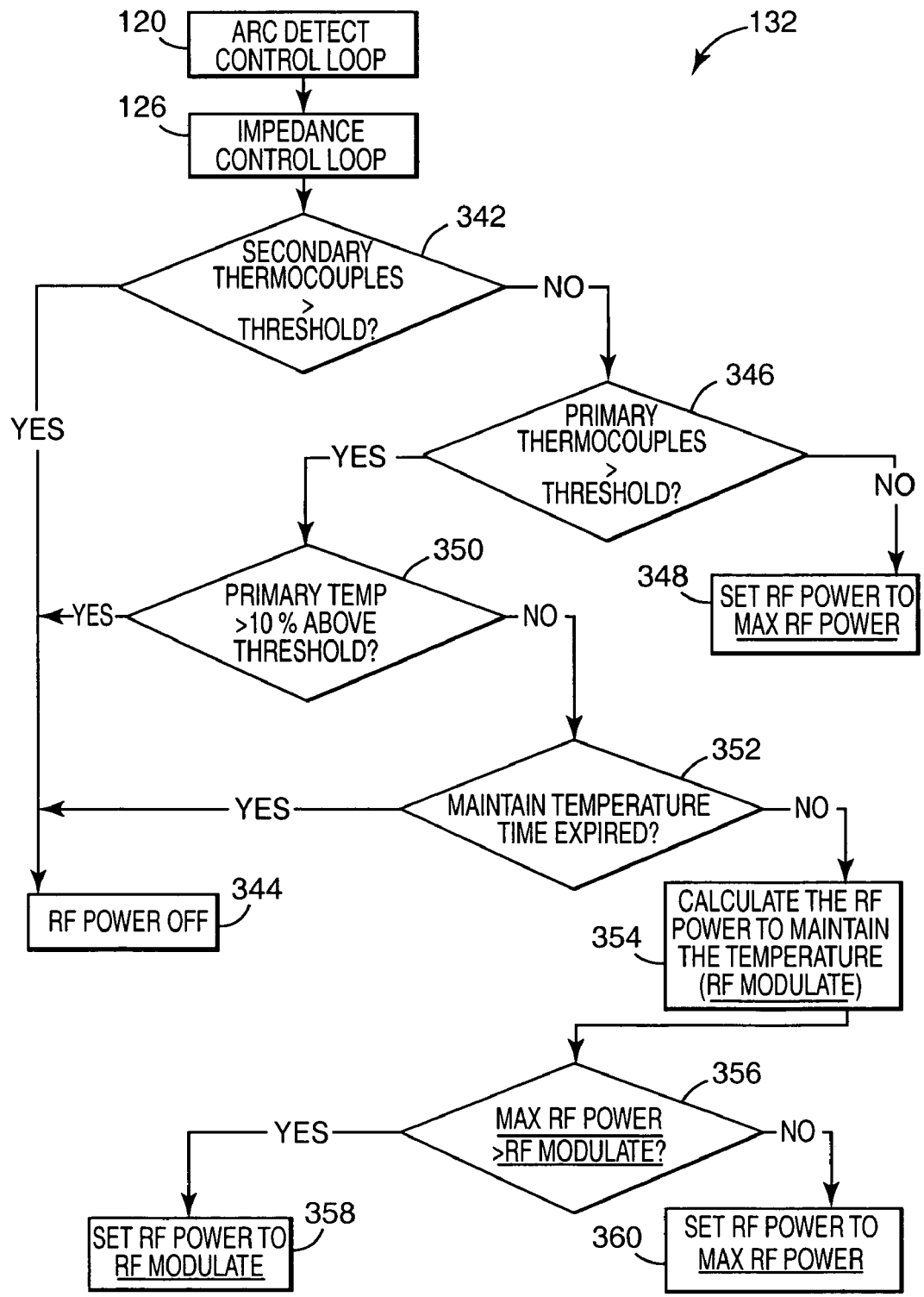
FIG. 15 illustrates a temperature control loop of an apparatus in accord with the present invention.

Referring now to FIG. 15, the Temperature Control Loop 132 will be described. Loop 132 will compare the temperatures measured by the secondary temperature sensors with the thresholds established for those secondary sensors at 342. As noted previously, these secondary sensors will normally be located at a distance away from current source. For example, where a needle electrode is being used to deliver current to the virtual electrode formed within a liver tumor having an approximate radius of 1.5 centimeters is being ablated, it may be desirable to have sensors located at distances of 2.0, 2.5 and 3.0 centimeters from the needle electrode. These sensors would ostensibly be located in healthy tissue. While some margin of healthy tissue destruction would be acceptable, that is, an ablation zone of 2 or 2.5 centimeters in radius, minimizing the amount of healthy tissue being ablated is also desirable. Monitoring of the temperatures of such tissue is preferred so as to be able to discontinue the ablation procedure when the maximum desired temperature for that tissue is reached. This will help insure that amount of healthy tissue that is ablated is kept to a minimum for a particular procedure. Thus, if a secondary temperature threshold is exceeded, the power will be discontinued as at 344. An additional function of measuring the temperatures with the secondary thermocouples is to insure that a lesion of a desired size is created. In addition, it may be desirable to place a secondary sensor at a position within the desired lesion to enable the ablation of the tissue within the zone where a lesion is desired to be created so as to monitor the progress of the ablation.

If the secondary temperature thresholds are not exceeded, the temperature measured by the primary sensor will be compared with the primary temperature threshold at 346. If the threshold is not exceeded, then the power level will be set to the maximum power level at 348. Where the primary threshold is exceeded or is within a certain predefined percentage of the threshold, the percentage will be calculated as at 350. Where the primary temperature exceeds the threshold by a predetermined amount, say 10%, then the power will be shut off as at 344. It should be noted that the primary and secondary thermocouples may be checked in any order. During operation of VETAD 10 such temperature checks will occur substantially simultaneously, but in any event more rapidly than the tissue will respond to RF power level changes.

When the primary temperature measurement does not exceed the predefined percentage then the time at the desired temperature will be determined and compared against the predetermined time that the temperature is to be maintained, which as noted may range from zero to about five minutes, with a typical nominal range of about thirty to about sixty seconds. That is, to ensure that the desired lesion is created and that the tissue is in fact dead, it is preferred that the temperature of the tissue at the primary thermocouple be maintained for a predefined time period. If the predefined time period has expired, then the power will be terminated as at 344. If the predetermined time period has not elapsed, then the power level necessary to maintain the temperature at the threshold will be calculated at 354 either using a proportional integral derivative method discussed below or the alternative process discussed below. The maximum power level will then be compared with this calculated power level, termed RF Modulate, at 356. If the maximum power level exceeds RF Modulate, the power will be set to equal RF Modulate at 358. That is, at 354–358 the power level needed to attain and maintain the primary threshold temperature is calculated and if that power level has not yet been reached, the generator will be instructed by microprocessor 20 to increase the power supplied to the surgical instrument 26 to that power level, or RF Modulate. If the maximum RF power level is less than RF Modulate, then the power level will be set to the maximum RF power as at 360. The maximum RF power is the maximum power level as calculated by the impedance control loop. This is the method by which the impedance control loop overrides the temperature control loop.

The use of a proportional integral derivative to calculate a value is a well known technique. Thus, during operation the VETAD 10 may perform a primary temperature control of RF power to reach and maintain a desired temperature at the primary thermocouple. This control is accomplished through the following described process. This process will utilize a variety of inputs, including the desired temperature at the primary thermocouple, the current or measured temperature at the primary thermocouple, elapsed time, the maximum impedance, the proportional gain $K_p$, the integral gain $K_i$, and the derivative gain $K_d$. With these inputs, the power level can be calculated as follows:

$$\text{Error\_Integral} = \sum_{o}^{n} \text{Error}(n)$$

where the following constraints are imposed:
1. predetermined minimum<Error_Integral<predetermined maximum
2. Freeze Error Integral if applied RF power is at Maximum RF power $$\text{Error\_derivative} = \text{Error}(n) - \text{Error}(n-1)$$

The output of this algorithm is ablation RF power and is computed as follows:

$$\text{Ablation\_RF\_Power} = (\max\_RF\_Power) * (\text{Error\_proportion}(n) * K_p + \text{Error\_Integral}/K_i + \text{Error\_derivative} * K_d)$$

This calculated RF power is constrained by the maximum impedance RF power as follows:

Ablation RF Power=the lower of the (calculated ablation RF power) and (maximum impedance RF power).

The generator will change the output RF power to the new ablation RF power. This calculation can be done as frequently as desired, such as once per second.

Alternatively, the RF power level required to hold the primary temperature at a desired temperature level can be determined as follows. First, the desired primary hold temperature $T_d$, that is, the temperature that is desired to be maintained to ensure first the creation of a lesion and second the creation of a lesion of a particular size, is specified either as a default or an input parameter. Temperatures currently measured $T_c$ by the primary thermocouple are then compared with the desired primary temperature $T_d$. As $T_c$ reaches the $T_d$ and then equals it, the RF power will be decreased a predetermined amount such as 50 percent. With each predetermined temperature increase, such as 0.5° C., then, the applied RF power can be reduced in additional predetermined increments, such as 50 percent. This routine can be followed until the applied power is reduced to one watt. As $T_c$ is reduced to below $T_d$, the applied RF power can be increased by a predetermined amount, such as 50 percent. Again, as the temperature continues to drop by a predetermined increment, the applied power can be increased by a predetermined amount. These temperature and power increase increments can also be 0.5° C. and 50 percent, respectively. The increments for both increasing and decreasing the RF power will depend on the distance of the location of the primary thermocouple from the current supplying electrode, which may be any specified distance. A distance of 0.5 centimeters has been found to be useful for example.

Table 8 illustrates the various parameters that can be used with the temperature control loop 132 and typical values that can be associated therewith.

TABLE 8

| PARAMETER | TYPICAL VALUE | LOCATION | DESCRIPTION |
| --- | --- | --- | --- |
| Primary Temp | 60 deg. C. | Surgical Instrument | This is the control temp. which the algorithm will try to maintain |
| Secondary Temp 1 | 45 deg. C. | Surgical Instrument | This is temp for one of safety thermocouples —temp > will cause ablation to end |
| Secondary Temp 2 | 45 deg. C. | Surgical Instrument | Safety Thermocouple |
| Secondary Temp 3 | 45 deg. C. | Surgical Instrument | Safety Thermocouple |
| Secondary Temp 4 | 45 deg. C. | Surgical Instrument | Safety Thermocouple |
| Secondary Temp 5 | 45 deg. C. | Surgical Instrument | Safety Thermocouple |
| Maintain Time | 1 minute | Surgical Instrument | Time to maintain primary temp once it is achieved |
| Overshoot % | 10% | Surgical Instrument/Table | Overshoot allowed on primary temp. > than this and ablation ends |
| Maximum Ablation Time | 10 min or less | Surgical Instrument and | Maximum ablation time. Upper limit of 10 minutes per |

TABLE 8-continued

| PARAMETER | TYPICAL VALUE | LOCATION | DESCRIPTION |
|---|---|---|---|
| | | Table/Hardware | generator, but smaller value may be programmed in Surgical Instrument |
| Max RF Power | variable | software variable | Maximum power that can be used by the Temperature Control Loop. Variable is controlled by the Impedance Control of RF Power Loop. |
| Voltage Clamp | 100 volts | Surgical Instrument | This is the maximum voltage that can be used in an ablation. Supersedes Max RF power (reaching Voltage Clamp may prevent Max Power from being delivered) |
| Auxiliary Thermocouple Present | No | Surgical Instrument | Informs generator if an Auxiliary Thermocouple will be used with the disposable. (Yes, No, or Optional) |

Figure 16:
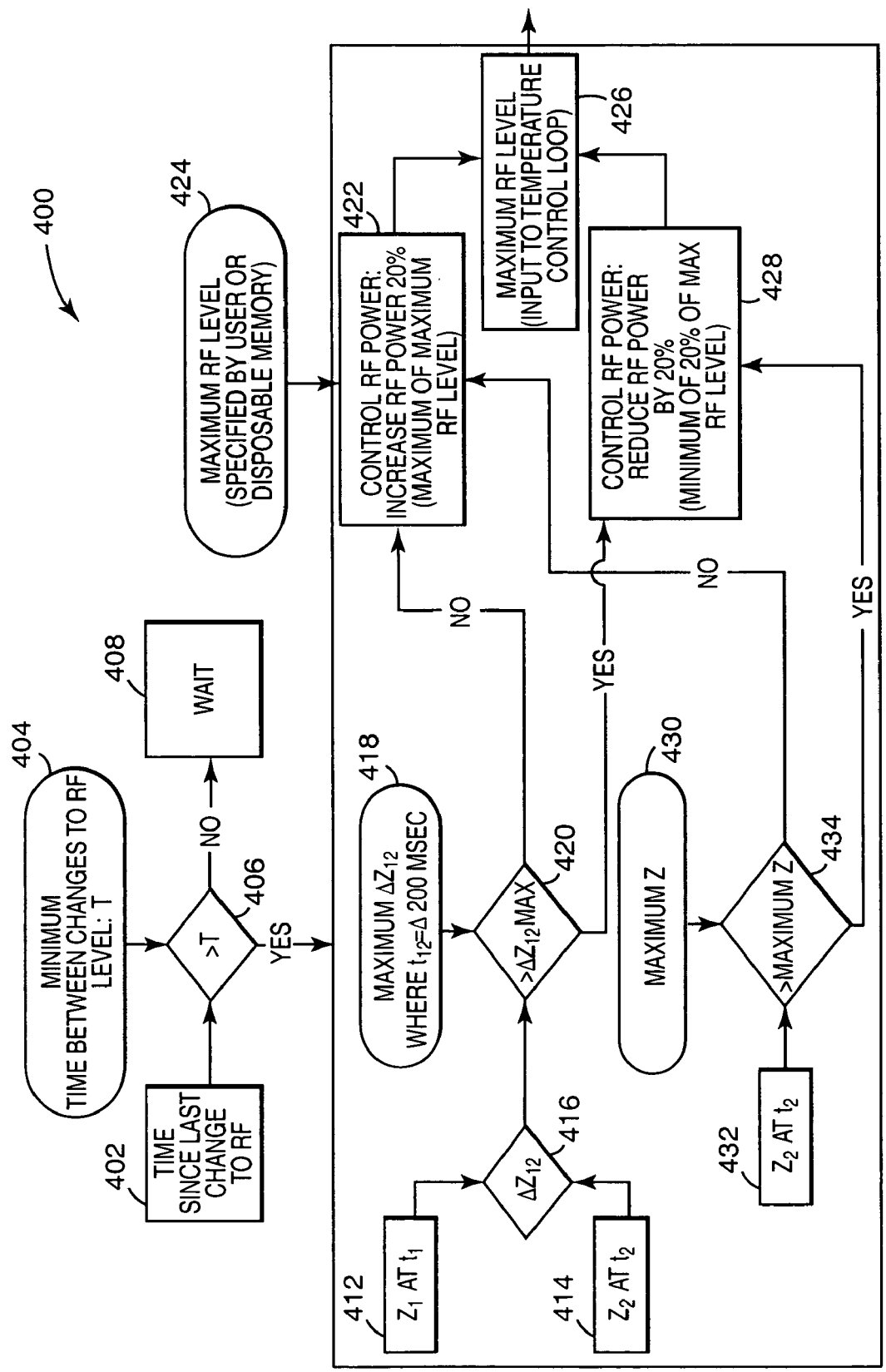
FIG. 16 illustrates a method in accord with the present invention using measured impedance to control the fluid flow rate and the applied power.

Operational control of VETAD 10 can be provided by impedance monitoring, temperature monitoring, or both. One example of an impedance monitoring loop is shown in FIG. 14, as has been discussed previously. A more detailed example of an impedance monitoring control loop is illustrated in FIG. 16. Preferably, impedance monitoring will include both rapid, transient spikes in the measured impedance within a predetermined time period as well as slower, yet continuous increases in the measured impedance within a longer period of time. Thus, VETAD 10 will monitor not only the absolute impedance measured at any one time, but also the rate of change in the impedance over at least one and preferably two time intervals of differing lengths to account for transient spikes in the impedance, due to factors such as air bubbles in the conductive fluid, as well as slower rises in the impedance, which may be indicative of the application of too much radio frequency power or a low fluid infusion rate.

Thus, as seen in FIG. 16, VETAD 10 will take frequent impedance measurements. The impedance control loop 400 will include determining the time since the RF power level was last changed as at 402. A predefined or default minimum time period between changes to RF power levels will be established as at 404. The time period 402 can then be compared with the predefined time period as at 406. If the time 402 is less than the predetermined minimum 404, then the apparatus 10 will enter a wait state as at 408. If the time 402 is greater than the minimum time T then the control loop 400 will enter the sub routine 410.

In subroutine 410 the impedance measurement circuit 90 (FIG. 3) will measure a first impedance $Z_1$ at a time $t_1$ at 412 and a second impedance $Z_2$ at a time $t_2$ as at 414. $Z_1$ and $Z_2$ will be compared at 416 to provide an impedance difference $\Delta Z_{12}$. Alternatively, several $\Delta Z_{12}$ values could be averaged to arrive at a calculated $\Delta Z_{12}$. A Maximum $\Delta Z_{12}$ over a predetermined time period, say 0.2 seconds or 200 milliseconds by way of example only, will be provided as a default as at 418. Alternatively, several $\Delta Z_{12}$ values could be averaged. The calculated $\Delta Z_{12}$ will be compared with the Maximum $\Delta Z_{12}$ as at 420. If the calculated $\Delta Z_{12}$ does not exceed the Maximum $\Delta Z_{12}$, then the RF power level may be increased by a predetermined amount, say twenty percent by way of example, of the Maximum RF Level as at 422, the Maximum RF Level being supplied by the operator or as an input provided by memory 42 of surgical instrument 26 as at 424. This newly calculated RF power level will be supplied as at 426 as an input to the Temperature Control Loop 132.

Where the calculated $\Delta Z_{12}$ exceeds the Maximum $\Delta Z_{12}$, then RF power may be controlled and hence reduced as at 428 by a predetermined amount, which by way of example may be twenty percent of the Maximum RF Level 424. This calculated reduced power level will be supplied as an input to the Temperature Control Loop 132 as at 426.

In addition, a maximum impedance $Z_{max}$ will be specified by the operator or the memory 42 as at 430. The measured impedance $Z_2$ at time $t_2$ at 432 will be compared against $Z_{max}$ as at 434. Where $Z_2$ is less than $Z_{max}$ the RF power level will be increased as at 422. Where $Z_2$ is greater than $Z_{max}$ the RF power level will be decreased as at 428.

Figure 17:
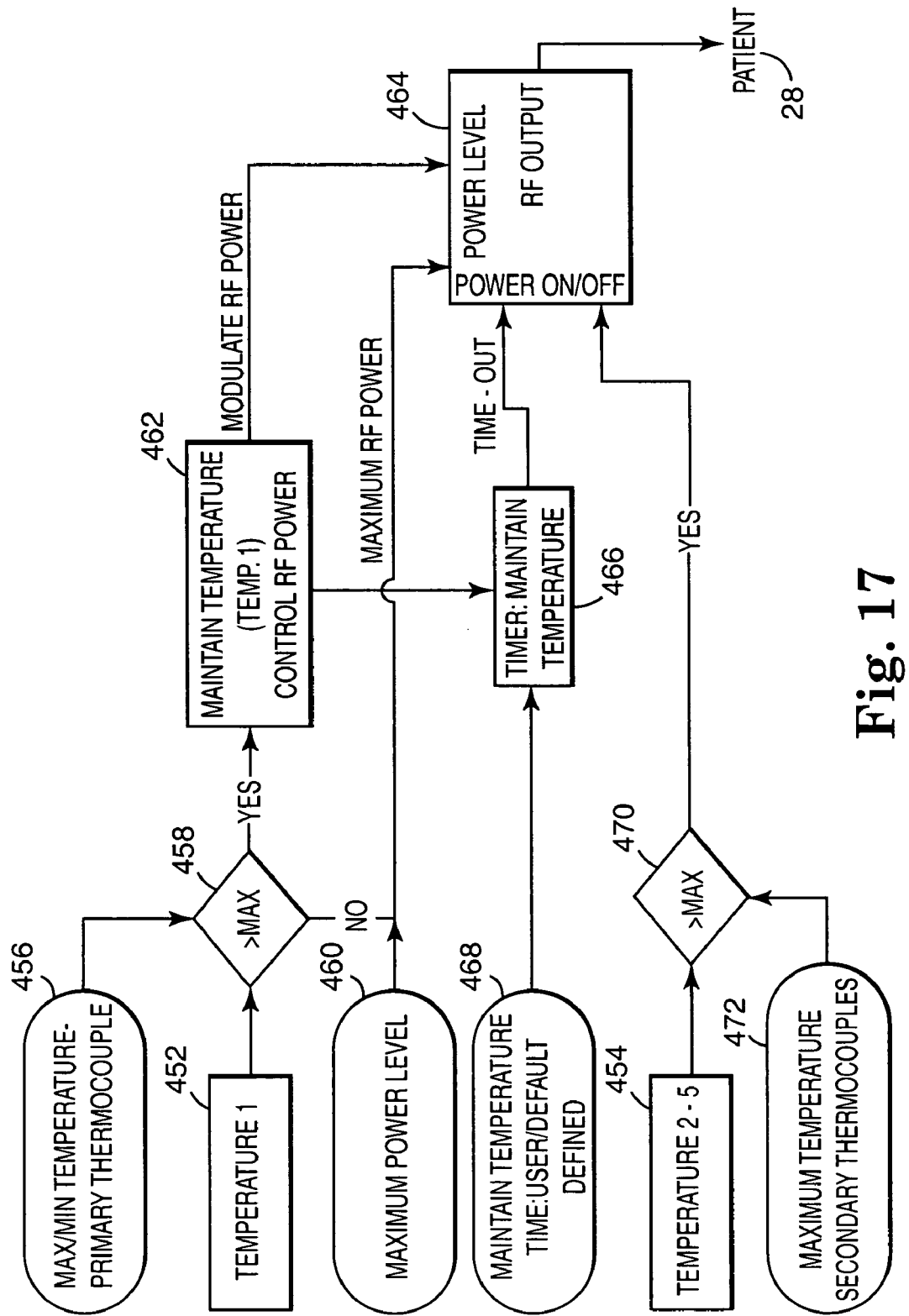
FIG. 17 illustrates a method in accord with the present invention using measured temperatures to control the fluid flow rate and the applied power.

A temperature control flow chart in accord with the present invention is illustrated in FIG. 17. As seen there, a plurality of thermocouples, including a primary and secondary thermocouples, are used to measure the tissue being ablated and the temperature of the tissues surrounding the tissue to be ablated. This method of creating a virtual electrode and controlling the application of radio frequency power to the patient will be operable in an automatic mode of operation of VETAD 10. Where VETAD 10 is operated in a manual mode of operation, the temperature control algorithm of the VETAD 10 will not operate except for the function of shutting off the application of radio frequency power to the patient if a maximum temperature threshold is exceeded.

Referring to FIG. 17, then, VETAD 10 will include a primary temperature control 450 as determined by the temperatures measured by the primary thermocouple 452 and the secondary thermocouples 454. In operation, VETAD 10 will increase the radio frequency power applied to the tissue to be ablated until either the temperature measured by the primary thermocouple reaches the predetermined temperature range required for the ablation of the tissue or until the predetermined maximum power level for the ablation procedure to be performed is reached, it being understood that different tissues may require differing levels of radio frequency power to accomplish the desired ablation. The temperature measured by primary thermocouple 452, which may be placed directly within the tissue to be ablated, will be compared against the predetermined maximum temperature 456 as indicated at 458.

If the measured temperature of the primary thermocouple is less than the maximum temperature for that thermocouple for that particular procedure, then the power will continue to be increased to the Maximum RF Power Level 460 as provided for the control loop 400 as indicated at 460. Where the temperature measured by the primary thermocouple equals or exceeds the maximum temperature for the procedure, then the achieved temperature will be maintained by controlling the applied power as at 462. Thus, if the achieved temperature exceeds the maximum temperature, the applied power will be modulated and the power will generally be reduced as necessary to bring the measured temperature at or just below the desired temperature. If the measured temperature is less than the minimum desired temperature, however, then the applied power will be increased. The power level will be set as at 464 for application to patient 28.

Once the preferred minimum temperature for the procedure is reached, the duration of the maintenance of that temperature will be compared as at 466 with default or user defined time period 468 for the temperature duration. That is, to ensure the creation of the desired lesion size and the consequent death of the desired tissue, the desired temperature should be maintained for a predetermined period of time based upon the time of tissue being ablated. Once the time period for the temperature maintenance has been achieved, then the radio frequency power will be turned off as indicated at 464. Alternatively, the temperature of the target tissue to be ablated can be increased to a predetermined temperature above the temperature for cell death and then the RF power can be discontinued. The latent heat in the tissue will be dissipated primarily by cell-to-cell conduction, thus ensuring that the cell death temperature will be exceeded by the target tissue for some period of time. Creation of the desired lesion size will then depend upon the temperature reached by the tissue.

If secondary thermocouples 454 are used to monitor the temperature of preselected tissue during the ablation procedure, then if any one of the temperature measurements exceeds its prescribed maximum as at 470 as input manually by the operator, held in memory 472 in VETAD 10, or held in memory 42 of surgical instrument 26, then the applied power will be discontinued as at 464. In this way, the size of the lesion can be controlled such that the minimum of healthy tissue is affected by the ablation procedure. Alternatively, certain procedures may allow the operator to reduce the applied RF power rather than discontinue it.

During a therapy procedure the physician may find it desirable to manually discontinue the application of RF power for preselected period of times, particularly when operating VETAD 10 in the manual mode. Thus a therapy can enter a "pause" mode that may be activated, for example, by release of the foot pedal 62 during RF treatment. The therapy can enter a "resume" mode wherein the application of RF power is reinitiated, for example, by re-pressing the foot pedal 62 within a predetermined period of time, for example, 15 seconds, after a "pause" was initiated.

Discontinuing the application of RF power will enable the patient's body to immediately begin to dissipate the heat built up in the tissue, thus cooling the tissue whose ablation is desired. This cooling effect will be particularly true where, as in most cases, the conductive fluid is allowed to continue to flow, thereby carrying heat away from the ablation site. If therapy is to be resumed, the dissipation of the heat during the pause should be accounted for to ensure that the therapy is successful. As has been discussed generally earlier, a maximum time period will generally be established for a particular procedure to ensure the safety of the patient. Thus, the time spent in the pause mode must be accounted for to ensure that an ablation procedure can be competed and to account for the heat dissipation. Several methods may be used to account for this time spent in the pause mode, including:

$$t_{resume} = 1.5 t_{pause} + t_{continue}$$

$$t_{resume} = t_{reheat} + t_{continue}$$

where:
- $t_{resume}$ = total RF time after therapy cycle, e.g., that is, the foot pedal, is reactivated until complete cycle is completed.
- $t_{pause}$ = time during "pause" mode
- $t_{reheat}$ = time to reach $T_{last}$ after therapy enters "resume" mode following a pause
- $t_{continue}$ = remaining time of RF to complete initial setting $t_{total}$
- $t_{total}$ = RF time setting for the therapy
- $t_{pre-pause}$ = RF time until "pause"
- $T_{last}$ = last temperature measured at selected tissue thermocouple before "pause"
- T = temperature measured at selected tissue thermocouple
- $T_{body}$ = body temperature The following conditions would be assumed:
If during $t_{pause}$, $T = T_{body}$, then restart at $t_{total}$; and
If $t_{reheat} + t_{Continue}$ reaches $t_{total}$, then RF power is shut off.

The first method of determining the time remaining in the therapy session for the application of RF power, $t_{resume}$, is to add the time spent during the pause mode, $t_{pause}$, plus a percentage thereof to the amount of time remaining to complete the original prescribed therapy, $t_{continue}$.

The second method shown above for determining the time remaining in the pause mode spent in the pause mode is to measure the time $t_{reheat}$ spent in reaching the last temperature $T_{last}$ recorded before RF power was discontinued once therapy has resumed and adding that time to the amount of time remaining to complete the original prescribed therapy, $t_{continue}$.

In addition, $t_{resume}$ could be determined as follows:

$$t_{resume} = t_{pause} + \text{(database library of time)}$$

where the "database library of time" comprises a table of experimental data of time to be added to the remaining "resume" time to provide an effective treatment based upon $t_{pause}$ time in relation to treatment cycle.

The first condition states that if the pause is so long that the tissue being ablated once again cools to body temperature, then the therapy cycle should begin anew with a complete time cycle. The second condition states that if the time to reheat the tissue to $T_{last}$ and the time remaining in the therapy, $t_{continue}$ is equal to the total time for the therapy then the therapy should be discontinued.

Either of the foregoing methods of determining the amount of time remaining $t_{resume}$ in the therapy cycle will aid in providing a safe and efficacious therapy for the patient where the physician decides for whatever to initiate an indeterminate halt in the application of RF power during a therapy session.

Figure 18:
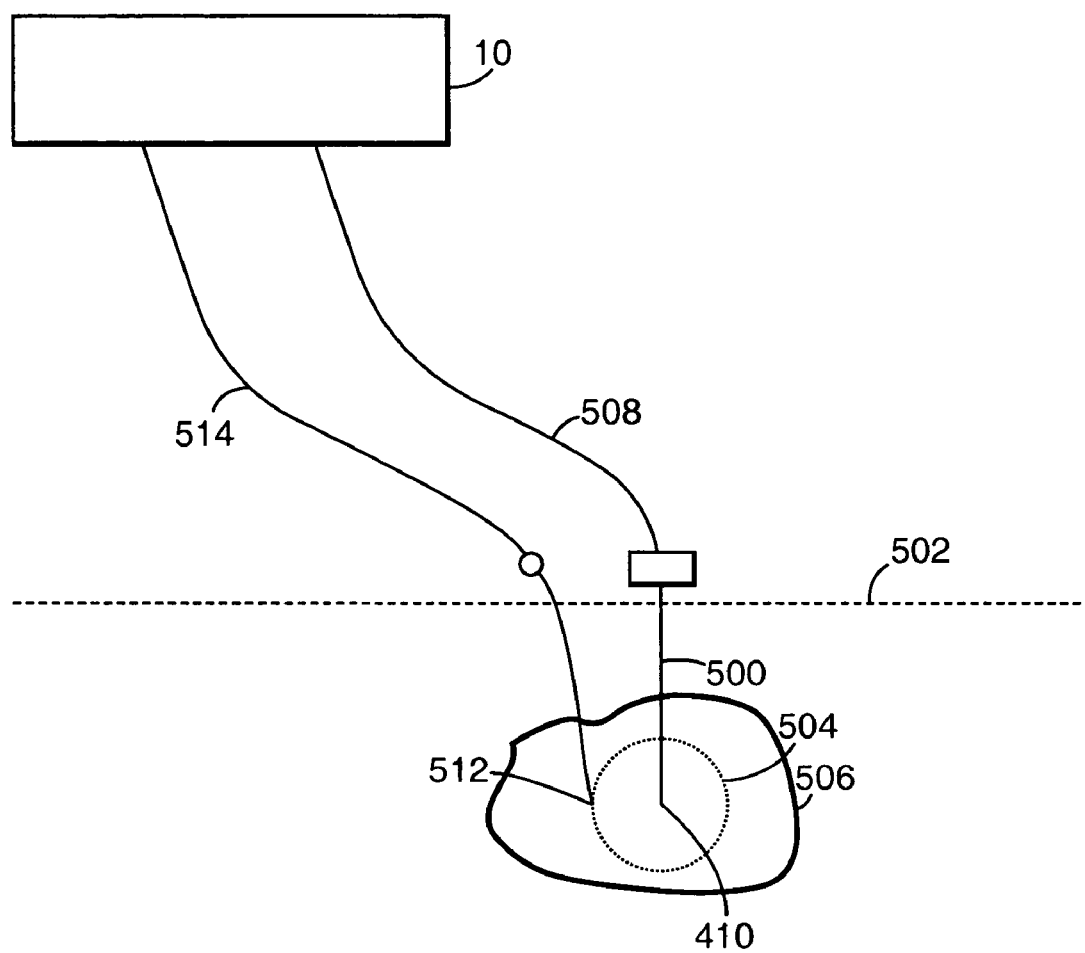
FIG. 18 illustrates the present invention in operation with respect to a patient.
Figure 19:
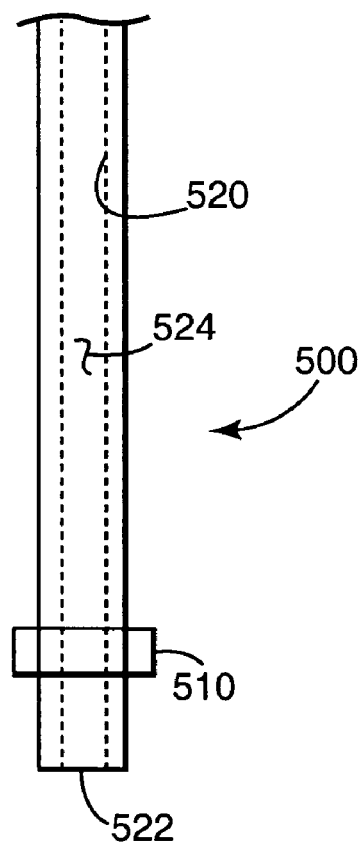
FIG. 19 shows an enlarged view of a surgical instrument useful with the present invention.
Figure 20:
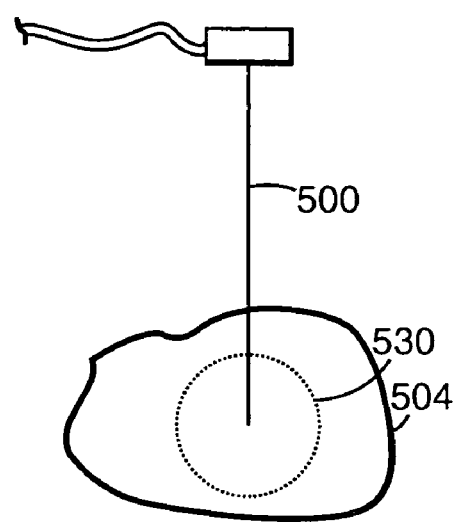
FIG. 20 shows a virtual electrode created by the present invention.

Referring now to FIGS. 18–20, the operation and method of the present invention will be explained more fully. FIGS. 18–20 are highly schematic illustrations and are meant to be exemplary the operation and method of the present invention. As seen in FIG. 18, a surgical instrument comprising a straight needle 500 has been inserted percutaneously, that is, through the skin 502, shown in phantom outline, into a tissue 504 to be ablated, for example, a liver metastases, in a patient's liver 506. Needle 500 will be fluidly and electrically connected to the VETAD 10 by a line 508. Needle 500 will preferably have a thermocouple 510 disposed at the distal end thereof. After placement of the needle 500 at the desired location, one or more additional thermocouples 512 may be placed to provide additional or secondary temperature monitoring and connected to VETAD 10 by a line 514. One or more of these thermocouples could be placed in the metastases 504 remote from the needle 500 or they could be placed in tissue surrounding the metastases.

Referring now to FIG. 19, an enlarged view of a needle useful with the present invention will be described. It will be observed that the needle 500 can be hollow, that is, include an interior lumen or passage 520 shown in phantom. The conductive fluid will be pumped through lumen 520 to one or more apertures 522, through which the conductive fluid may flow into the tissue to be ablated 504. As illustrated in the FIG., the needle 500 includes a single aperture 522 at the distal end thereof. Alternatively, the single distal aperture could be plugged and a plurality of apertures placed in the side surface 524 of the needle, or both. It will be understood that other surgical instruments can also be used with the present invention.

Once the needle has been placed within the tissue, the pre-ablation infusion of conductive fluid will begin. The infusion of the conductive fluid will create an interstitial virtual electrode. Referring to FIG. 20, then, it will be observed that the conductive fluid has permeated the tissue 504 interstitially so as to create a virtual electrode 530 shown in phantom. Once the desired level of pre-ablation infusion has occurred, or stated otherwise, once the desired virtual electrode size has been approximately achieved, the radio frequency current provided by the generator 18 will be applied to the tissue 504 through the needle 500, which serves as a metal electrode as well as a conductive fluid delivery port. The virtual electrode 530 may have a substantially spherical or oval shape; the exact configuration of the virtual electrode will depend upon factors such as tissue irregularities, channels between cells, and the direction in which the fluid flow is directed and any differential fluid flow in a particular direction, among others. The virtual electrode 530 will, as previously described, enable the applied current density to be spread over a large volume of tissue and thus will create a larger lesion than can be achieved with "dry" radio frequency power. The tissue ablation procedure will be controlled as previously described above. The conductive or electrolytic fluid will be supplied to the tissue throughout the ablation procedure, that is, at least as long as the RF current is being provided thereto.

It will be observed that the foregoing description of the present invention has spoken often and generally of measuring impedance. Impedance, as is well known, is the resistance to an alternating current between two locations along a current pathway. Generally speaking, the present invention measures the impedance between two locations within the apparatus 10 along the RF current pathway. Nevertheless, the resistance to the current flow between the apparatus and the virtual electrode and between the ground pad (or other return electrode where a bipolar instrument is used) and the apparatus forms a small, reasonably well known, and non-varying resistance that can be considered in the impedance measurements that are made. The impedance that varies is that between the tissue-virtual electrode interface and the tissue-ground pad interface, with the bulk of the impedance being at the tissue-virtual electrode interface. Thus, it will be understood that, in essence, it is the impedance at the tissue-virtual electrode interface that is monitored and of concern. By "considered" it is meant that the varying parameters relating to the impedance measurements can either be increased to account for the impedance along the current pathway at other than the tissue-virtual electrode interface, decreased, or set with that value in mind.

While the use of a straight needle as a surgical instrument has been shown and described, it will be understood that the present invention is not so limited. For example, a hollow helical needle as shown in U.S. Pat. No. 5,431,649 to Mulier, et al. could also be used with the present invention. In addition, the present invention could also be used with surface devices such as forceps or a rollerball, as known in the art. As noted, the interconnection of the disposable surgical instrument 26 with the VETAD 10 can be "coded" with the number of active pins such that the VETAD 10 can recognize and identify the particular surgical instrument being used according to its programming and establish predetermined default parameters for use of a particular instrument 26 or the instrument 26 can include a memory chip holding default operating parameters that are provided to the microprocessor 20 when the instrument 26 is queried by the microprocessor. The present invention is thus not limited to a single type of surgical instrument. A surgical instrument useful with the present invention, however, will be able to deliver a conductive fluid to a desired ablation site as well as a radio frequency current.

The present invention has been noted as being able to use saline as a conductive fluid. The present invention is not so limited, however, and other conductive solutions that are not toxic in the amounts to be used during an ablation procedure may also be used therewith. In addition, contrast fluids such as Hypaque™ may be used in connection with other conductive fluids to provide the ability to image the creation, control, and operation of the virtual electrode during a procedure.

As previously noted the present invention finds use with conductive or electrolytic solutions. As an example, saline in either its isotonic or hypertonic form has been found to be useful in the RF ablation process. Desirably, the solution used during an RF procedure should include a conductive medium and a buffer to provide a proper PH. In addition, a solution used in accord with the present invention could include a contrast media to allow fluoroscopic imaging of the virtual electrode and a preservative to extend the shelf life of any prepared solution. Finally where a malignancy is being ablated, a cytotoxin could be added to the solution to enhance the tissue killing effects of the ablation process.

Reference can be made to Table 9 below, which shows various components of an RF ablation solution that may satisfy the foregoing criteria. Preferably, an RF ablation solution will have an initial impedance of greater than or about 200 ohms at room temperature. As noted previously in the discussion of how an RF ablation process is carried out, as RF energy is applied to the tissue through the electrolytic solution, the tissue begins to heat. Desirably, as the temperature of the solution rises, the impedance of the solution will decrease. A decrease to an impedance level of less than 100 ohms at the termination of the procedure is desirable. The decrease in impedance allows greater coupling of RF ablating energy to the tissue as the temperature rises. This in turn enables the ablation process to be carried out more rapidly than if the impedance of the conductive fluid remained constant or nearly so as the temperature increased.

Reducing the time for the ablation process to be carried out is desirable from a clinic standpoint to minimize the effects of the process on the patient.

Referring to the tables below, it should be understood that the formulations appearing in Table 9 are representative of the various types of chemicals that can be used in an RF ablating solution and are not meant to indicate that the particular chemicals shown therein must be used in a horizontal fashion across the table. Stated otherwise for example, an RF ablating solution may include an electrolyte comprising one of sodium chloride, sodium bicarbonate, or magnesium chloride; one of a cytotoxin comprising barium chloride, cisplatin or alcohol; a contrast agent comprising one of any generally acceptable iodine product, hypaque, omnipaque, or conray; a buffer, if necessary, such as hydrogen chloride; and if necessary, a stabilizer such as propylene glycol. It will be understood that where the RF ablating solution is not being used to ablate malignancies that the cytotoxin would in most instances be neither necessary nor desirable. Such uses would include ablation of prostate tissue or other tissue where no malignancy was indicated and surface rather than interstitial ablation of tissues in such procedures as, lung volume reduction, anuloplasty, treatment of vascular abnormalities such as but not limited to aneurysm, arteriovenous malformations, fistulas, sterilization procedures through closure of the fallopian tubes, and treatment of varicose veins.

Referring now to Table 10, specific formulations of RF ablating solutions are shown for particular tissue being treated. It will be understood that the relative concentrations of each of the chemical components forming the solution can be varied and fall generally within a broadly acceptable range. For example, the concentration of the electrolyte itself can vary from isotonic saline at 0.9% to hypertonic saline at up to 37%. For example, where the tumor being treated is greater than 3.5 centimeters in diameter, hypertonic saline is useful in the treatment. Where the tumor size is generally 1 centimeter or less, isotonic saline can be used as the electrolyte. For tumors falling within the range of about 1 centimeter to about 3.5 centimeters the concentration of the saline can vary between isotonic and hypertonic concentrations. As previously noted, generally it is desirable to have a reduction in impedance of the RF ablating solution of at least 50% from the start of the procedure to its termination. Thus, the concentrations of the various components of the RF ablating solution are desirably adjusted so as to provide the desired impedance drop as well as perform the necessary functions for which they are provided. Thus, for example, where alcohol is being used as the cytotoxic agent the concentration of the electrolyte will desirably be increased since alcohol itself is a poor conductor and will adversely affect the impedance performance of the solution otherwise.

TABLE 9

| Electrolyte | Cytotoxin | Contrast Agent | Buffer | Stabilizer |
|---|---|---|---|---|
| NaCl | BaCl | Iodine generally | HCl | Propylene glycol |
| Na(CO$_3$)$_2$ | Cisplatin | Hypaque | | |
| MgCl | Alcohol | Omnipaque | | |
| | | Conray | | |

TABLE 10

| Tissue | Electrolyte | Cytotoxin | Contrast Medium | Buffer | Stabilizer/Preservative |
|---|---|---|---|---|---|
| Tumor 3.5 cm | Hypertonic NaCl | BaCl | Iodine | HCl | CaNa$_2$ |
| 1 cm Tumor 3.5 cm | | | | HCl | |
| Tumor 1 cm | Isoasmotic NaCl | Cisplatin | | HCl | Propylene glycol |
| Strabismus | Isoasmotic NaCl | Not applicable | Not applicable | HCl | Propylene glycol |
| Liver | NaCl | Not applicable | Not applicable | HCl | CaNa$_2$ |
| Lung | Isoasmotic NaCl | Not applicable | Not applicable | HCl | CaNa$_2$ |

The present invention has been described relative to an apparatus illustrated with a single fluid supply. As previously noted, however, the present invention could include a plurality of such fluid administration systems. For example, a separate fluid supply/pump system for the administration of an insulating fluid such as dextrose could be provided. This fluid would be provided to tissue whose ablation was not desired. The dextrose would substantially prevent current transfer to that tissue thereby preventing its ablation. Alternatively, a chilled fluid could be provided to tissue whose ablation was not desired. In such a circumstance the chilled fluid would act as a heat sink to carry heat away from such tissue. The administration of the chilled or insulated fluid would also be controlled by the microprocessor 20 according to predetermined parameters. Also, several fluid sources may be used to apply independently varying flow rates to different locations on a more complex electrode configuration. In addition, where fluid is being supplied to tissue through a needle having one or more small apertures, such apertures can become clogged or plugged, leading to the termination of the procedure due to a high impedance condition developing. Supplying fluid to multiple needles from multiple fluid sources will lessen the likelihood that such a high impedance condition will develop and that the procedure will have to be terminated. Thus, in summary, the present invention contemplates a plurality of fluid pumps, such as syringe pumps or flexible tube pumps, controlled by microprocessor 20, each pump connected to a separate fluid supply so as to provide the physician with the ability to administer a variety of fluids during an ablation procedure.

It will further be understood that while the present invention has been described as being used only relative to a liver metastases, that it is not so limited. Thus, the present invention may be useful for ablating cardiac tissue responsible for irregular heartbeats and for treatment of benign prostate hypertrophy. In addition to liver metastases, other neoplasms, such as breast, lung, and prostate cancer may also be treated in accord with the present invention. It may also be used in the treatment of vascular disease including arteriovenous malformations and aneurysms. In addition, the present invention may be used to treat soft tissue, such as the lung, where a reduction in lung volume is desired, and solid organs and tissues, among them bone.

Additionally, it will be understood that the present invention is useful with either a monopolar or bi-polar electrode. Thus, where a monopolar electrode is used, a ground electrode will be placed in contact with the patient as is well known in the prior art to provide a complete circuit for the applied radio frequency current. That is, the ground electrode will be connected to the apparatus 10 and the current will travel from the generator 18 to the surgical instrument 26, then through the patient to the ground electrode and back to the apparatus 10. Where a bipolar electrode is used the current path will be from the apparatus to the surgical instrument to the patient and then back to the surgical instrument and the apparatus.

Finally, it will be understood that the present invention can be used to treat both human and non-human patients.

The present invention having thus been described, other modifications, alterations, or substitutions may now suggest themselves to those skilled in the art, all of which are within the spirit and scope of the present invention. It is therefore intended that the present invention be limited only by the scope of the attached claims below.

What is claimed is:

1. A system for ablating tissue, comprising:
   a surgical instrument including an ablation element for delivery of an ablating energy to the tissue;
   a RF generator coupled to the surgical instrument to deliver ablating energy to the ablation element;
   a memory chip coupled to the surgical instrument and storing predetermined time limit information for at least one operating parameter of the surgical instrument; and
   a processor for receiving the predetermined time limit information for the at least one operating parameter and increasing a current value of the operating parameter after the predetermined time limit has elapsed.

2. The system of claim 1, wherein the memory chip is programmed with a second operating parameter including the number of times the surgical instrument is used and the processor is adapted to limit the number of times the surgical instrument is used based upon the second operating parameter.

3. The system of claim 1, wherein the operating parameter relates to the delivery of ablating energy.

4. The system of claim 3, wherein the processor is adapted to limit the amount of the ablating energy delivered to the surgical instrument based upon the operating parameter.

5. The system of claim 3, wherein the processor is programmed to limit the total amount of time that must expired prior to the ablating energy being delivered to the surgical instrument based upon the operating parameter.

6. The system of claim 1, wherein the processor is programmed to establish a time limit within which the surgical instrument must be used.

7. The system of claim 1, wherein the memory chip is pre-programmed.

8. The system of claim 1, wherein the memory chip is a microchip.

9. The system of claim 1, wherein the memory chip is located in a connector used to couple the surgical instrument to the processor.

10. The system of claim 1, wherein the surgical instrument further includes a temperature sensor for sensing a temperature.

11. The system of claim 10, wherein the operating parameter relates to temperature.

12. The system of claim 1, further comprising a source of conductive fluid selectively providing conductive fluid to the tissue.

13. The system of claim 12, wherein the operating parameter relates to fluid flow.

14. The system of claim 1, wherein the memory chip is adapted to provide a second operating parameter and the second operating parameter is an identifier unique to the surgical instrument.

15. A system for ablating tissue, comprising:
    a surgical instrument including an ablation element for delivery of an ablating energy to the tissue;
    a RF generator coupled to the surgical instrument to deliver ablating energy to the ablation element; and
    an identifying means coupled to the surgical instrument and the RF generator, the identifying means programmed to provide at least one predetermined time limit designating an elapsed time required prior to changing an identifying characteristic of the surgical instrument to a non-zero value.

16. The system of claim 15, wherein the identifying characteristic is an operating parameter.

17. The system of claim 16, wherein the identifying means is configured to further provide a second operating parameter used to limit the number of times the surgical instrument is used.

18. The system of claim 16, wherein the operating parameter relates to the delivery of ablating energy.

19. The system of claim 18, wherein the identifying means is programmed to establish a time limit and initiate delivery of the ablating energy to the surgical instrument upon expiration of the time limit.

20. The system of claim 18, wherein the operating parameter is used to limit the total amount of time the ablating energy is delivered to the surgical instrument.

21. The system of claim 16, wherein the identifying means is configured to further provide a second operating parameter used to limit the amount of time within which the surgical instrument must be used.

22. The system of claim 15, wherein the identifying means is a memory chip.

23. The system of claim 22, wherein the memory chip is pre-programmed.

24. The system of claim 22, wherein the memory chip is a microchip.

25. The system of claim 15, wherein the identifying means includes a memory chip located in a connector.

26. The system of claim 15, wherein the surgical instrument further includes a temperature sensor for sensing a temperature.

27. The system of claim 26, wherein the identifying characteristic relates to temperature.

28. The system of claim 15, further comprising a source of conductive fluid selectively providing conductive fluid to the tissue.

29. The system of claim 28, wherein the identifying characteristic relates to fluid flow.

30. The system of claim 15, wherein the identifying means is configured to further provide an identifier unique to the surgical instrument.

31. A method of treating tissue by ablation, the method comprising:
    providing an RF generator for the delivery of an ablating energy;
    connecting a surgical instrument to the RF generator, the surgical instrument comprising an ablation element for delivery of the ablating energy to tissue and a memory chip storing a predetermined time limit for an operating parameter;
    placing the surgical instrument in contact with tissue to be ablated;
    delivering the operating parameter from the memory chip to the RF generator;
    delivering ablating energy from the RF generator through the surgical instrument to tissue to be ablated based upon the operating parameter;

changing a value of the operating parameter following the elapse of the predetermined time limit while maintaining the surgical instrument relative to the tissue; and operating the surgical instrument to continue ablating the tissue.

32. The method of claim 31, wherein the memory chip delivers a second operating parameter that limits the number of times ablating energy is delivered from the RF generator through the surgical instrument.

33. The method of claim 31, wherein the memory chip delivers a second operating parameter that limits the total amount of time ablating energy is delivered from the RF generator through the surgical instrument.

34. The method of claim 31, further comprising establishing a time limit within which the surgical instrument may be used to deliver ablating energy.

35. The method of claim 31, wherein the operating parameter limits the delivery of ablating energy from the RF generator through the surgical instrument.

36. The method of claim 31, wherein the memory chip is pre-programmed.

37. The method of claim 31, wherein the memory chip is a microchip.

38. The method of claim 31, wherein the memory chip is located in a connector used to connect the surgical instrument to the RF generator.

39. The method of claim 31, wherein the surgical instrument further comprises a temperature sensor.

40. The method of claim 39, wherein the operating parameter limits the delivery of ablating energy from the RF generator based on temperature.

41. The method of claim 31, further comprising selectively providing conductive fluid to the tissue to be ablated from a source of conductive fluid.

42. The method of claim 41, further comprising controlling the flow of fluid from the source of conductive fluid to the tissue based upon the operating parameter.

43. The method of claim 31, wherein the memory chip delivers a second operating parameter that is an identifier unique to the surgical instrument.

* * * * *